US006399386B1

(12) United States Patent
Kirschner et al.

(10) Patent No.: US 6,399,386 B1
(45) Date of Patent: Jun. 4, 2002

(54) METHOD OF ISOLATING RECEPTOR AND LIGAND DNA

(75) Inventors: Marc W. Kirschner, Newton, MA (US); Noriyuki Kinoshita, Tokyo (JP)

(73) Assignee: President and Fellows of Harvard College, Cambridge, MA (US)

(*) Notice: Subject to any disclaimer, the term of this patent is extended or adjusted under 35 U.S.C. 154(b) by 0 days.

(21) Appl. No.: 09/507,773

(22) Filed: Feb. 18, 2000

Related U.S. Application Data

(60) Division of application No. 08/776,207, filed as application No. PCT/US95/09172 on Jul. 19, 1995, now Pat. No. 6,080,718, which is a continuation-in-part of application No. 08/279,217, filed on Jul. 22, 1994, now Pat. No. 5,573,944.

(51) Int. Cl.$^7$ .............................................. C12N 15/74
(52) U.S. Cl. ..................................................... 435/471
(58) Field of Search ........................... 435/7, 458, 468, 435/471

(56) References Cited

U.S. PATENT DOCUMENTS

| 5,238,916 A | 8/1993 | Goldfarb et al. ............... 514/2 |
| 5,256,643 A | 10/1993 | Persico et al. ................ 514/12 |
| 5,264,557 A | 11/1993 | Salomon et al. ............ 530/399 |

FOREIGN PATENT DOCUMENTS

| GB | 2223495 A | 4/1990 |
| JP | 04036184 | 2/1992 |
| WO | 89/04832 | 6/1989 |
| WO | 92/13948 | 8/1992 |
| WO | 93/19096 | 9/1993 |
| WO | 94/13796 | 6/1994 |

OTHER PUBLICATIONS

Hanks, Steven K., "Eukaryotic Protein Kinases," *Current Opinion in Structural Biology*, 1:369–383 (1991).

Fett, James W. et al., "Isolation and Characterization of Angiogenin, an Angiogenic Protein from Human Carcinoma Cells," *Biochemistry*, 24(20):5480–5486 (1985).

Maes, P. et al., "The Complete Amino Acid Seqence of Bovine Milk Angiogenin," *FEBS Letters*, 241(1,2):41–45 (1988).

Haugg and Schein, "The DNA Sequences of the Human and Hamster Secretory Ribonucleases Determined with the Polymerase Chain Reaction (PCR)," *Nucleic Acids Research*, 20(3):612 (1992).

Ciccodicola, Alfredo et al., "Molecular Characterization of a Gene of the 'EGF Family' Expressed in Undifferentiated Human NTERA2 Teratocarcinoma Cells," *The EMBO Journal*, 8(7):1987–1991 (1989).

Dono, Rosanna et al., "The Murine Cripto Gene: Expression During Mesoderm Induction and Early Heart Morphogenesis," *Development*, 118:1157–1168 (1993).

Basilico and Moscatelli, "The FGF Family of Growth Factors and Oncogenes," *Adv. Cancer Res.*, 59:115–165 (1992).

Cheng and Flanagan, "Identification and Cloning of ELF–1, a Developmentally Expressed Ligand for the Mek 4 and Sek Receptor Tyrosine Kinases," *Cell*, 79:157–168 (1994).

Flanagan and Leder, "The kit Ligand: A Cell Surface Molecule Altered in Steel Mutant Fibroblasts," *Cell*, 63:185–194 (1990).

Carlson, Marian et al., "The Secreted Form of Invertase in *Saccharomyces cerevisiae* Is Synthesized from mRNA Encoding a Signal Sequence," *Molecular and Cellular Biology*, 3(3):439–447 (1983).

Musci, Thomas J. et al., "Regulation of the Fibroblast Growth Factor Receptor in Early Xenopus Embryos," *Proc. Natl. Acad Sci. USA*, 87:8365–8369 (1990).

Elledge, Stephen J. et al., "λYES: A Multifunctional cDNA Expression Vector for the Isolation of Genes by Complementation of Yeast and *Escherichia coli* Mutations," *Proc. Natl. Acad. Sci. USA*, 88:1731–1735 (1991).

Amaya, Enrique et al., "Expression of a Dominant Negative Mutant of the FGF Receptor Disrupts Mesoderm Formation in Xenopus Embryos," *Cell*, 66:257–270 (1991).

Gallwitz, D. et al., "The Actin Gene in Yeast *Saccharomyces Cerevisiae*: 5' and 3' End Mapping, Flanking and Putative Regulatory Sequences," *Nucleic Acids Research*, 9:6339–6350 (1981).

Kimelman, David et al., "The Presence of Fibroblast Growth Factor in the Frog Egg: Its Role as a Natural Mesoderm Inducer," *Science*, 242:1053–1056 (1988).

Isaacs, H.V. et al., "Expression of a Novel FGF in the Xenopus Embryo. A New Candidate Inducing Factor for Mesoderm Formation and Anteroposterior Specification," *Development*, 114:711–720 (1992).

Tannahill, D. et al., "Developmental Expression of the Xenopus int–2 (FGF–3) Gene: Activation by Mesodermal and Neural Induction," *Development*, 115:695–702 (1992).

Joseph, Loren J. et al., "Complete Nucleotide and Deduced Amino Acid Sequences of Human and Murine Preprocathepsin L. An Abundant Transcript Induced by Transformation of Fibroblasts," *J. Clin. Invest.*, 81:1621–1629 (1988).

(List continued on next page.)

*Primary Examiner*—John Ulm
(74) *Attorney, Agent, or Firm*—Hamilton, Brook, Smith & Reynolds, P.C.

(57) ABSTRACT

Disclosed herein are compositions and methods which are useful in the identification and isolation of components involved in transmembrane receptor-mediated signaling. Such components include the receptors themselves (e.g., tyrosine kinase receptors, cytokine receptors and tyrosine phosphatase receptors), as well as ligands which bind the receptors and modulators of the downstream intracellular catalytic event which characterizes receptor-mediated signalling. Two novel ligands for the FGF receptor and the nucleotide sequences encoding them are also described.

4 Claims, 14 Drawing Sheets

OTHER PUBLICATIONS

Gal and Gottesman, "Isolation and Sequence of a cDNA for Human Pro–(Cathepsin L)," *Biochem. J.*, 253:303–306 (1988).

Kay, Brian K. et al., "Protential for Two Isoforms of the A1 Ribonucleoprotein in *Xenopus laevis*," *Proc. Natl. Acad. Sci. USA*, 87:1367–1371 (1990).

Kim and Baker, "Isolation of RRM–Type RNA–Binding Protein Genes and the Analysis of Their Relatedness by Using a Numerical Approach," *Molecular and Cellular Biology*, 13(1):174–183 (1993).

Wilson, R. et al., "2.2 Mb of Contiguous Nucleotide Sequence from Chromosome III of *C. elegans*," *Nature*, 368:32–38 (1994).

Hao, Qian–Lin et al., "Isolation and Sequence Analysis of a Novel Human Tyrosine Kinase Gene," *Molecular and Cellular Biology*, 9(4):1587–1593 (1989).

Johnson, Daniel E. et al., "Diverse Forms of a Receptor for Acidic and Basic Fibroblast Growth Factors," *Molecular and Cellular Biology*, 10:4728–4736 (1990).

Nieuwkoop and Faber (editors), "The Further Development of the Intestinal Tract and Glands," "External and Internal Stage Criteria in the Development of *Xenopus Laevis*," *Normal Table of Xenopus Laevis* (Daudin), pp. 160–170, North–Holland Publishing Company, Amsterdam (1956).

Lyons and Nelson, "An Immunological Method for Detecting Gene Expression in Yeast Colonies," *Proc. Natl. Acad. Sci USA*, 81:7426–7430 (1984).

Kornbluth, S. et al., "Novel Tyrosine Kinase Identified by Phosphotyrosine Antibody Screening of cDNA Libraries," *Molecular and Cellular Biology*, 8(12):5541–5544 (1988).

Figure 1B
Gal specific positives
E: 65 colonies
X: 29 colonies
Repeat of screen with aniti-PTyr
E: 9 colonies
X: 2 colonies
Rescue plasmid DNA
Retransformation into a yeast strain not expressing FGFR
Is activation of P-Tyr by plasmid FGFR dependent?
FGFR dependent P-Tyr:   E: 8 genes , X: 2 genes
FGFR independent P-Tyr:   E: 1 gene,   X: 0

ALP cDNA

```
ACCAAAAGAA CGACAGAACG AAGGAAAGAC AGAGACAGTC CTTGTTTTAA GACTCCAGGG      60
GAATTTACGT CTAATAAAGA GAAGAGAGGC ATTGTATGCT TGACATTATG GTGGCAGTTT     120
TATCTTCTCT GTTGACAATT TGCATTATCC TCAGCTTTTC TCTCCATCC GATACCCAGA      180
ATATCAATGC CTTTATGGAA AAGCACATTG TTAAGGAAGG AGCTGAAACA AACTGCAACC     240
AAACCATCAA AGACAGAAAC ATCCGGTTTA AAAACAACTG CAAATTCCGC AACACCTTTA     300
TTCATGATAC CAATGGTAAA AAGGTGAAGG AGATGTGCGC TGGGATTGTC AAATCTACCT     360
TTGTGATCAG CAAGGAACTG CTGCCTCTCA CTGACTGCTT GTTGATGGGA CGTACTGCAA     420
GACCCCCAAA TTGTGCTTAT AATCAAACAA GAACAACTGG GGTCATTAAT ATCACTTGTG     480
AAAACAATTA CCCTGTGCAC TTTGCTGGGT ACAAATCAAG CTTCTGTGCT TCATATTCTC     540
CATGTGCCTT AATAGTAATA ACTGTTTTCC TGCTCAGCCA GCTACTGCTC CCTGCTATGA     600
GATGATGCCC AGAAACGGGA GTATCAATAG CTAAAACTAG AAGGACTGAT AGTGATGGAT     660
GATTGTTCCT AAGTCATTTA GAGATCTACC TGTGTTCACT TCCAAACAAA GAAGACATAG     720
GTATAATTGA ATCAACCGTG ACATAGACTG ACTTCTAAAT AATAAAAGCA ACATTTTCTG     780
TTTTAACAAA AAAAAAAAAA AAAAAAAA                                       809
```

Figure 3

ALP
MLDIMVAVLSSLLTICIILSFSLPSDTQNINAFMEKHIV
KEGAETNCNQTIKDRNIRFKNNCKFRNTFIHDTNGKKVK
EMCAGIVKSTFVISKELLPLTDCLLMGRTARPPNCAYNQ
TRTTGVINITCENNYPVHFAGYKSSFCASYSPCALIVIT
VFLLSQLLLPAMR

Figure 4

```
                         *                   *      *
MLDIMVAVLSSLLTICIILSFSLPSDTQNINAFMEKHIVKEGAETN----CNQTIKDRNIRFKNN
                         AQDDYRYIHFLTQHYDAKPKGRNDE-YCFNMKNRRTRP---
                         VQPSLGKESAAMK FERQHMDSTVATSSSPTYCNQMKRRNMTQGQE

**  ****      *                                *     *  *  *
CKDRNTFIHG NKNDIKAICEDRN-GQPYRGDLRI-SKSEFQITICKHKGGSSRPP-CRYGATED-
CKFRNTFIHDTNGKKVKEMCAGI-VKSTFVISKEL----LPLTDCLLMGRTARPPNCAYNQTRT-
CKPVNTFVHESLAD-VHAVCSQENVKCKNGKSNCYKSHSALHITDCRLKGNAKYP-NCDY-QTSQH

**   ****    ****
SRVIVVGCENG--LPVHFDESFITRPH                bovine angiogenin (28.8%)
TGVINITCENN--YPVHFAGYKSSFCASYSPCALIVITVFLLSQLLLPAMR   Xenopus ALP
QKHIIVACEGNPFVPVHFDATV                     Chinese Hamster pancreatic RNase (32.3%)
```

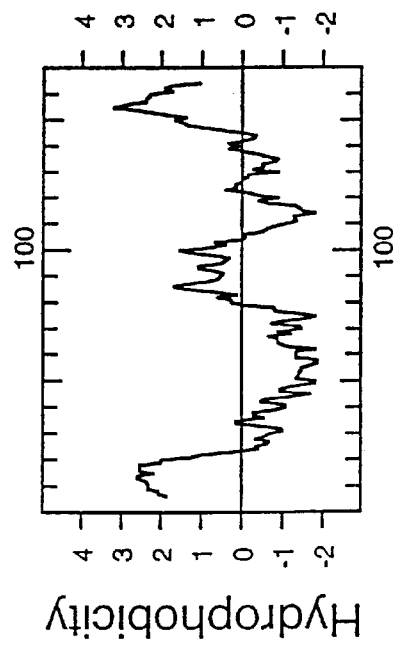

Figure 5

CLP cDNA

```
ATTTACCACC GACCGTTACA CCTGGTTTTT GCTAAGGACA CATTCAATAC AAGAACTAAA      60
AGTGGGAAAC TGGGGCCTTT GCAGAAAACA ATGCAGTTTT TAAGATTTCT TGCCATCCTT     120
ATTTTCTCTG CTAAACATTT TATCAAGCAT TGCAAGGTG AAACTTGCAT GGGACTGAAC      180
TGTAATGACC CAAGGTTATT GGAGGCAATT AAGAGCAACA CAATCAATCA GCTCTTGCAT    240
GATACAATTA ATGCCACCCA TGGAAAGAGT CCACCAAAAT CCACTAAAAC CTTGCCCTTC    300
TTGGGTATCA CAGACAGTAA GAAATTGAAT AGAAAATGCT GTCAGAATGG AGGCACTTGT   360
TTCTTGGGGA CCTTTTGCAT CTGCCCTAAG CAATTTACTG GTCGGCACTG TGAACATGAA   420
AGGAGGCCAG CAAGCTGCTC CGGTGTTCCC CATGGAGACT GGATCCGTCA GGGCTGCTTG   480
CTGTGTAGAT GTGTGTCTGG TGTCCTACAC TGCTTCAAGC CCGAGTCTGA GGACTGTGAT   540
GTTGTGCATG AAAAAAACAT GAGATCGGGG GTCCCGAGAA TGCAGCTCAG CTTAATCATC   600
TATTGCTTCC TTACTGCAAA CTTGTTTTAC CACATAGTTT GGCATCTGAA TATTGGACTT   660
TAACAGAGTA ACTTGAGTCT GCCAGTCAGG TTCAGATTGC AGACGTCTGT GTCTACACTG   720
CACTTTCAAT TTGTGAACCC ATTTTGCCAG GATTATGCTT GAAGTATATG GCTATCTTCC   780
ACCCCTGGAA TCCTGGAAAA TATGCAGAAA CTATACAATG CCTTATTTCT ATTGGTTGTT   840
TCATAAAATA ACTTTTTTTA TAGGATGATG TGTATAGTGG CCAGAATGGG TTTACAGTAC   900
TTCCAAGCAC TGGCGTTGGT TCAAAATAGC TACTGGGTTC TTGCTCTTTG CTGCATGTTG   960
AGATCAGGAA GCTAGTCTTA TACTTACCCA GTGCATTCTG TATATATGTA AATTTTATTA  1020
ACTTATTAGA CACGTTGTAC ATTAACAGCA TCCTTCACAA ACTTTATTT TTTTTAATT    1080
TTTTTATTAA TTGACAAAGA GAACAAAGTA TCTAGGAACA TTTTACAAAT ATTGTCCTAC  1140
TACATTGCAT GTTGTGGTTC TTGTTTGTAT GTTTGTCCTG ATCTTCTACA ATGTATCCCT  1200
AGCCATAAAA CGATTTTGTG AGTGTGTGTG TGTGACTGCA TCCCATTTTA TTCATTATGC  1260
AAACACTTTG CAAATGATTG TGCAGCAATG TAAGTGCTAG CCTGTGGTCA ACAGTGCTGA  1320
ATGTAAATCT TGGAGCGGTG ATATCAGCAT GCTTATGGAG GCTCAATAAC CTTGGTCTTG  1380
CCCCTTTAAA TTCTATTTTT CTACGGGCAA GTAAATCTAA ACTGGTAAAG TACCTTCTTT  1440
TAAGGAAATG AATCACTGAA TGTTATAATT CCAGTTTCAG GCCACAGACA ATTAATGACA  1500
GCTCAGGGAA TAATACAATT GCCCATGTTT GATGCACCTA ATGTACTGTA TGTATTACAG  1560
GGTGTCTGCT TGATGTTTGC AATGAAGACA TTAAATACTG TACCTAAAAG AAAAAAAAA   1620
AAAAAAAAAA AAA                                                     1633
```

Figure 6

CLP
MQFLRFLAILIFSAKHFIKHCKGETCMGLNCNDPRLLEA
IKSNTINQLLHDTINATHGKSPPKSTKTLPFLGITDSKK
LNRKCCQNGGTCFLGTFCICPKQFTGRHCEHERRPASCS
GVPHGDWIRQGCLLCRCVSGVLHCFKPESEDCDVVHEKN
MRSGVPRMQLSLIIYCFLTANLFYHIVWHLNIGL

Figure 7

```
                  MQFLRFLAILIFSAKHFIKHCKGETCMGLNCNDPRLLEAIKSNTINQLLHDTINATHGKSPP
                                        MGYFSSSVVLLVAISSAFEFGPVAGRDLAIRDNSIWDQKEPAVRD
 *      ***   * *  *****  **  ***          **  *     ****  *****     ***

KSTKTLPFLGITDSKKLNRKCCQNGGTCFLGTFCICPKQFTGRHCEHERRPASCSGVPHGDWIRQGCLLCRCVSGVLHCF
RSFQFVPSVGIQNSKSLNKTCCLNGGTCILGSFCACPPSFYGRNCEHDVRKEHCGSILHGTWLPKKCSLCRCWHGQLHCL
 *  *  *   *  *  *  * *** **  * *       *    *   * **      *         *** *  **

KPESEDCDVVHEKNMRSGVPRMQLSLIIYCFLTANLFYHIVWHLNIGL   Xenopus CLP
PQTFLPGCDGHVMDQDLKASRTPCQTPSVTTFML                mouse cripto
```

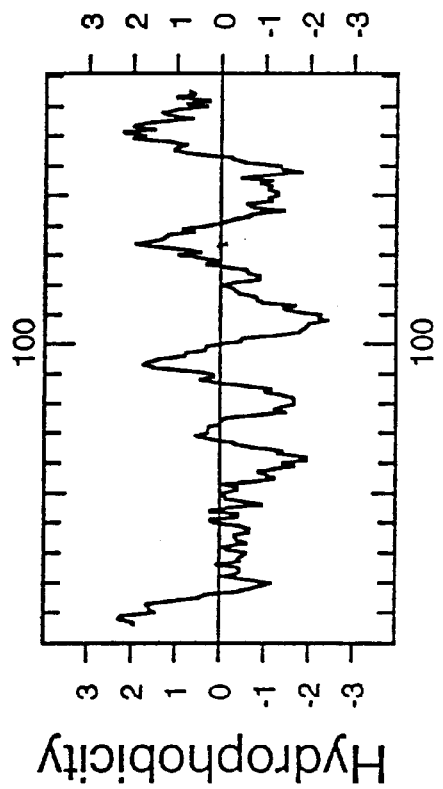

Figure 8

Figure 10B (CLP)                        ↓
MQFLRFLAILIFSAKHFIKHCKGETCMGLNCNDPRLLEAI    40
KSNTINQLLHDTINATHGKSPPKSTKTLPFLGITDSKKLN    80
RKCCQNGGTCFLGTFCICPKQFTGRHCEHERRPASCSGVP   120
HGDWIRQGCLLCRCVSGVLHCFKPESEDCDVVHEKNMRSG   160
VPRMQL<u>SLIIYCFLTANLFYHIVWHLNIGL</u>              190

(ALP)                        ↓
MLDIMVAVLSSLLTICIILSFSLPSDTQNINAFMEKHIVK    40
EGAETNC<u>N</u>QTIKDRNIRFKNNCKFRNTFIHDTNGKKVKEM    80
CAGIVKSTFVISKELLPLTDCLLMGRTARPPNCAY<u>N</u>QTRT   120
TGVI<u>N</u>ITCENNYPVHFAGYKSSFCASYSPCA<u>LIVITVFLL</u>   160
<u>SQLLLPAMR</u>                                  169 arrow; predicted cleavage sites
<u>N</u>: predicted N-glycosilation sites

Hydrophobic regions at C-terminus are underlined

Figure 11

FRL-1
MQFLRFLAILIFSAKHFIKHCKGETCMGLNCNDPRLLEA

IKSNTINQLLHDTINATHGKSPPKSTKTLPFLGITDSKK

\*  \* \*  \*      \* \*      \*  \*
LNRKCCQNGGTCFLGTFCICPKQFTGRHCEHERRPASCS

\*         \* \*  \*
GVPHGDWIRQGCLLCRCVSGVLHCFKPESEDCDVVHEKN

MRSGVPRMQLSLIIYCFLTANLFYHIVWHLNIGL

\*: amino acid residues highly conserved among EGF repeats

Figure 12

SEQUENCE LISTING

<160> NUMBER OF SEQ ID NOS: 18

<210> SEQ ID NO 1
<211> LENGTH: 809
<212> TYPE: DNA
<213> ORGANISM: Xenopsus laevis

<400> SEQUENCE: 1

```
accaaaagaa cgacagaacg aaggaaagac agagacagtc cttgttttaa gactccaggg      60
gaatttacgt ctaataaaga gaagagaggc attgtatgct tgacattatg gtggcagttt     120
tatcttctct gttgacaatt tgcattatcc tcagcttttc tctcccatcc gatacccaga     180
atatcaatgc ctttatggaa aagcacattg ttaaggaagg agctgaaaca aactgcaacc     240
aaaccatcaa agacagaaac atccggttta aaaacaactg caaattccgc aacacccttta    300
ttcatgatac caatggtaaa aaggtgaagg agatgtgcgc tgggattgtc aaatctacct     360
ttgtgatcag caaggaactg ctgcctctca ctgactgctt gttgatggga cgtactgcaa     420
gaccccaaa ttgtgcttat aatcaaacaa gaacaactgg ggtcattaat atcacttgtg      480
aaaacaatta ccctgtgcac tttgctgggt acaaatcaag cttctgtgct tcatattctc     540
catgtgcctt aatagtaata actgtttttcc tgctcagcca gctactgctc cctgctatga    600
gatgatgccc agaaacggga gtatcaatag ctaaaactag aaggactgat agtgatggat     660
gattgttcct aagtcatttta gagatctacc tgtgttcact tccaaacaaa gaagacatag    720
gtataattga atcaaccgtg acatagactg acttctaaat aataaaagca acattttctg     780
ttttaacaaa aaaaaaaaaa aaaaaaaa                                        809
```

<210> SEQ ID NO 2
<211> LENGTH: 169
<212> TYPE: PRT
<213> ORGANISM: Xenopus laevis

<400> SEQUENCE: 2

Met Leu Asp Ile Met Val Ala Val Leu Ser Ser Leu Leu Thr Ile Cys
 1               5                  10                  15

Ile Ile Leu Ser Phe Ser Leu Pro Ser Asp Thr Gln Asn Ile Asn Ala
            20                  25                  30

Phe Met Glu Lys His Ile Val Lys Glu Gly Ala Glu Thr Asn Cys Asn
        35                  40                  45

Gln Thr Ile Lys Asp Arg Asn Ile Arg Phe Lys Asn Asn Cys Lys Phe
    50                  55                  60

Arg Asn Thr Phe Ile His Asp Thr Asn Gly Lys Lys Val Lys Glu Met
65                  70                  75                  80

Cys Ala Gly Ile Val Lys Ser Thr Phe Val Ile Ser Lys Glu Leu Leu
                85                  90                  95

Pro Leu Thr Asp Cys Leu Leu Met Gly Arg Thr Ala Arg Pro Pro Asn
            100                 105                 110

Cys Ala Tyr Asn Gln Thr Arg Thr Thr Gly Val Ile Asn Ile Thr Cys
        115                 120                 125

Glu Asn Asn Tyr Pro Val His Phe Ala Gly Tyr Lys Ser Ser Phe Cys
    130                 135                 140

Ala Ser Tyr Ser Pro Cys Ala Leu Ile Val Ile Thr Val Phe Leu Leu
145                 150                 155                 160

Ser Gln Leu Leu Leu Pro Ala Met Arg
                165

<210> SEQ ID NO 3
<211> LENGTH: 1633
<212> TYPE: DNA
<213> ORGANISM: Xenopus Laevis

<400> SEQUENCE: 3
atttaccacc gaccgttaca cctggttttt gctaaggaca cattcaatac aagaactaaa      60
agtgggaaac tggggccttt gcagaaaaca atgcagtttt aagatttct tgccatcctt     120 attttctctg ctaaacattt tatcaagcat tgcaaaggtg aaacttgcat gggactgaac     180
tgtaatgacc caaggttatt ggaggcaatt aagagcaaca caatcaatca gctcttgcat     240
gatacaatta atgccaccca tggaaagagt ccaccaaaat ccactaaaac cttgcccttc     300
ttgggtatca cagacagtaa gaaattgaat agaaaatgct gtcagaatgg aggcacttgt     360
ttcttgggga cctttgcat ctgccctaag caatttactg gtcggcactg tgaacatgaa     420
aggaggccag caagctgctc cggtgttccc catggagact ggatccgtca gggctgcttg     480
ctgtgtagat gtgtgtctgg tgtcctacac tgcttcaagc ccgagtctga ggactgtgat     540
gttgtgcatg aaaaaaacat gagatcgggg gtcccgagaa tgcagctcag cttaatcatc     600
tattgcttcc ttactgcaaa cttgttttac cacatagttt ggcatctgaa tattggactt     660
taacagagta acttgagtct gccagtcagg ttcagattgc agacgtctgt gtctacactg     720
cactttcaat tgtgaaccc attttgccag gattatgctt gaagtatatg ctatcttcc     780 acccctggaa tcctggaaaa tatgcagaaa ctatacaatg ccttatttct attggttgtt     840
tcataaaata actttttta taggatgatg tgtatagtgg ccagaatggg tttacagtac     900

-continued

```
ttccaagcac tggcgttggt tcaaaatagc tactgggttc ttgctctttg ctgcatgttg    960
agatcaggaa gctagtctta tacttaccca gtgcattctg tatatatgta aattttatta   1020
acttattaga cacgttgtac attaacagca tccttcacaa acttttattt tttttttaatt   1080 tttttattaa ttgacaaaga gaacaaagta tctaggaaca ttttacaaat attgtcctac   1140
tacattgcat gttgtggttc ttgtttgtat gtttgtcctg atcttctaca atgtatccct   1200
agccataaaa cgattttgtg agtgtgtgtg tgtgactgca tcccatttta ttcattatgc   1260
aaacactttg caaatgattg tgcagcaatg taagtgctag cctgtggtca acagtgctga   1320
atgtaaatct tggagcggtg atatcagcat gcttatggag gctcaataac cttggtcttg   1380
cccctttaaa ttctattttt ctacgggcaa gtaaatctaa actggtaaag taccttcttt   1440
taaggaaatg aatcactgaa tgttataatt ccagtttcag gccacagaca attaatgaca   1500
gctcagggaa taatacaatt gcccatgttt gatgcaccta atgtactgta tgtattacag   1560
ggtgtctgct tgatgtttgc aatgaagaca ttaaatactg tacctaaaag aaaaaaaaaa   1620
aaaaaaaaaa aaa                                                     1633
```

<210> SEQ ID NO 4
<211> LENGTH: 190
<212> TYPE: PRT
<213> ORGANISM: Xenopus laevis

<400> SEQUENCE: 4

```
Met Gln Phe Leu Arg Phe Leu Ala Ile Leu Ile Phe Ser Ala Lys His
  1               5                  10                  15

Phe Ile Lys His Cys Lys Gly Glu Thr Cys Met Gly Leu Asn Cys Asn
                 20                  25                  30

Asp Pro Arg Leu Leu Glu Ala Ile Lys Ser Asn Thr Ile Asn Gln Leu
             35                  40                  45

Leu His Asp Thr Ile Asn Ala Thr His Gly Lys Ser Pro Pro Lys Ser
         50                  55                  60

Thr Lys Thr Leu Pro Phe Leu Gly Ile Thr Asp Ser Lys Lys Leu Asn
 65                  70                  75                  80

Arg Lys Cys Cys Gln Asn Gly Gly Thr Cys Phe Leu Gly Thr Phe Cys
                 85                  90                  95

Ile Cys Pro Lys Gln Phe Thr Gly Arg His Cys Glu His Glu Arg Arg
                100                 105                 110

Pro Ala Ser Cys Ser Gly Val Pro His Gly Asp Trp Ile Arg Gln Gly
            115                 120                 125

Cys Leu Leu Cys Arg Cys Val Ser Gly Val Leu His Cys Phe Lys Pro
        130                 135                 140

Glu Ser Glu Asp Cys Asp Val Val His Glu Lys Asn Met Arg Ser Gly
145                 150                 155                 160

Val Pro Arg Met Gln Leu Ser Leu Ile Ile Tyr Cys Phe Leu Thr Ala
                165                 170                 175

Asn Leu Phe Tyr His Ile Val Trp His Leu Asn Ile Gly Leu
            180                 185                 190
```

<210> SEQ ID NO 5
<211> LENGTH: 124
<212> TYPE: PRT
<213> ORGANISM: Bovine

<400> SEQUENCE: 5

Ala Gln Asp Asp Tyr Arg Tyr Ile His Phe Leu Thr Gln His Tyr Asp

```
              1               5                  10                 15
Ala Lys Pro Lys Gly Arg Asn Asp Glu Tyr Cys Phe Asn Met Met Lys
                        20                  25                  30

Asn Arg Arg Thr Arg Pro Cys Lys Asp Arg Asn Thr Phe Ile His Gly
            35                  40                  45

Asn Lys Asn Asp Ile Lys Ala Ile Cys Glu Asp Arg Asn Gly Gln Pro
        50                  55                  60

Tyr Arg Gly Asp Leu Arg Ile Ser Lys Ser Glu Phe Gln Ile Thr Ile
65                  70                  75                  80

Cys Lys His Lys Gly Ser Ser Arg Pro Pro Cys Arg Tyr Gly Ala
                        85                  90                  95

Thr Glu Asp Ser Arg Val Ile Val Val Gly Cys Glu Asn Gly Leu Pro
                100                 105                 110

Val His Phe Asp Glu Ser Phe Ile Thr Arg Pro His
            115                 120
```

<210> SEQ ID NO 6
<211> LENGTH: 131
<212> TYPE: PRT
<213> ORGANISM: Chinese Hamster

<400> SEQUENCE: 6

```
Val Gln Pro Ser Leu Gly Lys Glu Ser Ala Met Lys Phe Glu Arg
1               5                   10                  15

Gln His Met Asp Ser Thr Val Ala Thr Ser Ser Pro Thr Tyr Cys
                    20                  25                  30

Asn Gln Met Met Lys Arg Arg Asn Met Thr Gln Gly Gln Glu Cys Lys
            35                  40                  45

Pro Val Asn Thr Phe Val His Glu Ser Leu Ala Asp Val His Ala Val
        50                  55                  60

Cys Ser Gln Glu Asn Val Lys Cys Lys Asn Gly Lys Ser Asn Cys Tyr
65                  70                  75                  80

Lys Ser His Ser Ala Leu His Ile Thr Asp Cys Arg Leu Lys Gly Asn
                        85                  90                  95

Ala Lys Tyr Pro Asn Cys Asp Tyr Gln Thr Ser Gln His Gln Lys His
                100                 105                 110

Ile Ile Val Ala Cys Glu Gly Asn Pro Phe Val Pro Val His Phe Asp
            115                 120                 125

Ala Thr Val
        130
```

<210> SEQ ID NO 7
<211> LENGTH: 160
<212> TYPE: PRT
<213> ORGANISM: Mus musculus

<400> SEQUENCE: 7

```
Met Gly Tyr Phe Ser Ser Val Val Leu Val Ala Ile Ser Ser
1               5                   10                  15

Ala Phe Glu Phe Gly Pro Val Ala Gly Arg Asp Leu Ala Ile Arg Asp
                    20                  25                  30

Asn Ser Ile Trp Asp Gln Lys Glu Pro Ala Val Arg Asp Arg Ser Phe
            35                  40                  45

Gln Phe Val Pro Ser Val Gly Ile Gln Asn Ser Lys Ser Leu Asn Lys
        50                  55                  60

Thr Cys Cys Leu Asn Gly Gly Thr Cys Ile Leu Gly Ser Phe Cys Ala
```

```
65                  70                  75                  80

Cys Pro Pro Ser Phe Tyr Gly Arg Asn Cys Glu His Asp Val Arg Lys
                85                  90                  95

Glu His Cys Gly Ser Ile Leu His Gly Thr Trp Leu Pro Lys Lys Cys
            100                 105                 110

Ser Leu Cys Arg Cys Trp His Gly Gln Leu His Cys Leu Pro Gln Thr
        115                 120                 125

Phe Leu Pro Gly Cys Asp Gly His Val Met Asp Gln Asp Leu Lys Ala
    130                 135                 140

Ser Arg Thr Pro Cys Gln Thr Pro Ser Val Thr Thr Thr Phe Met Leu
145                 150                 155                 160

<210> SEQ ID NO 8
<211> LENGTH: 150
<212> TYPE: PRT
<213> ORGANISM: Homo sapien

<400> SEQUENCE: 8

Met Ala Ala Gly Ser Ile Thr Thr Leu Pro Ala Leu Pro Glu Asp Gly
1               5                   10                  15

Gly Ser Gly Ala Phe Pro Pro Gly His Phe Lys Asp Pro Lys Arg Leu
                20                  25                  30

Tyr Cys Lys Asn Gly Gly Phe Phe Leu Arg Ile His Pro Asp Gly Arg
            35                  40                  45

Val Asp Gly Val Arg Glu Lys Ser Asp Pro His Ile Lys Leu Gln Leu
        50                  55                  60

Gln Ala Glu Glu Arg Gly Val Val Ser Ile Lys Gly Val Cys Ala Asn
65                  70                  75                  80

Arg Tyr Leu Ala Met Lys Glu Asp Gly Arg Leu Leu Ala Ser Lys Cys
                85                  90                  95

Val Thr Asp Glu Cys Phe Phe Phe Glu Arg Leu Glu Ser Asn Asn Tyr
            100                 105                 110

Asn Thr Tyr Arg Ser Arg Lys Tyr Thr Ser Trp Tyr Val Ala Leu Lys
        115                 120                 125

Arg Thr Gly Gln Tyr Lys Leu Gly Ser Lys Thr Gly Pro Gly Gln Lys
    130                 135                 140

Ala Ile Leu Phe Leu Pro
145                 150

<210> SEQ ID NO 9
<211> LENGTH: 149
<212> TYPE: PRT
<213> ORGANISM: Bovine

<400> SEQUENCE: 9

Met Ala Glu Gly Glu Thr Thr Thr Phe Thr Ala Leu Thr Glu Lys Phe
1               5                   10                  15

Asn Leu Pro Leu Gly Asn Tyr Lys Lys Pro Lys Leu Leu Tyr Cys Ser
                20                  25                  30

Asn Gly Gly Tyr Phe Leu Arg Ile Leu Pro Asp Gly Thr Val Asp Gly
            35                  40                  45

Thr Lys Asp Arg Ser Asp Gln His Ile Gln Leu Gln Leu Cys Ala Glu
        50                  55                  60

Ser Ile Gly Glu Val Tyr Ile Lys Ser Thr Glu Thr Gly Gln Phe Leu
65                  70                  75                  80

Ala Met Asp Thr Asp Gly Leu Leu Tyr Gly Ser Gln Thr Pro Asn Glu
```

```
                        85                  90                  95
Glu Cys Leu Phe Leu Glu Arg Leu Glu Glu Asn His Tyr Asn Thr Tyr
                    100                 105                 110

Ile Ser Lys Lys His Ala Glu Lys His Trp Phe Val Gly Leu Lys Lys
            115                 120                 125

Asn Gly Arg Ser Lys Leu Gly Pro Arg Thr His Phe Gly Gln Lys Ala
        130                 135                 140

Ile Leu Phe Leu Pro
145

<210> SEQ ID NO 10
<211> LENGTH: 206
<212> TYPE: PRT
<213> ORGANISM: Homo sapiens

<400> SEQUENCE: 10

Met Ser Gly Pro Gly Thr Ala Ala Val Ala Leu Leu Pro Ala Val Leu
 1               5                  10                  15

Leu Ala Leu Leu Ala Pro Trp Ala Gly Arg Gly Gly Ala Ala Ala Pro
            20                  25                  30

Thr Ala Pro Asn Gly Thr Leu Glu Ala Glu Leu Glu Arg Arg Trp Glu
        35                  40                  45

Ser Leu Val Ala Leu Ser Leu Ala Arg Leu Pro Val Ala Ala Gln Pro
50                  55                  60

Lys Glu Ala Ala Val Gln Ser Gly Ala Gly Asp Tyr Leu Leu Gly Ile
65                  70                  75                  80

Lys Arg Leu Arg Arg Leu Tyr Cys Asn Val Gly Ile Gly Phe His Leu
                85                  90                  95

Gln Ala Leu Pro Asp Gly Arg Ile Gly Gly Ala His Ala Asp Thr Arg
                100                 105                 110

Asp Ser Leu Leu Glu Leu Ser Pro Val Glu Arg Gly Val Val Ser Ile
            115                 120                 125

Phe Gly Val Ala Ser Arg Phe Phe Val Ala Met Ser Ser Lys Gly Lys
        130                 135                 140

Leu Tyr Gly Ser Pro Phe Phe Thr Asp Glu Cys Thr Phe Lys Glu Ile
145                 150                 155                 160

Leu Leu Pro Asn Asn Tyr Asn Ala Tyr Glu Ser Tyr Lys Tyr Pro Gly
                165                 170                 175

Met Phe Ile Ala Leu Ser Lys Asn Gly Lys Thr Lys Lys Gly Asn Arg
                180                 185                 190

Val Ser Pro Thr Met Lys Val Thr His Phe Leu Pro Arg Leu
            195                 200                 205

<210> SEQ ID NO 11
<211> LENGTH: 187
<212> TYPE: PRT
<213> ORGANISM: Xenopus laevis

<400> SEQUENCE: 11

Met Thr Val Pro Ser Ala Leu Val Pro Ile Leu Leu Leu Gly Thr Ala
 1               5                  10                  15

Ala Val Met Val Gln Cys Leu Pro Leu Ser Phe Gln Arg Asn Asp Thr
            20                  25                  30

Val Glu Arg Arg Trp Glu Thr Leu Phe Ser Arg Ser Met Gly Glu Lys
        35                  40                  45

Lys Asp Thr Ser Arg Asp Ser Asp Tyr Leu Leu Gly Ile Lys Arg Gln
```

-continued

```
                50                  55                  60
Arg Arg Leu Tyr Cys Asn Val Gly Ile Gly Phe His Ile Gln Val Leu
 65                  70                  75                  80

Pro Asp Gly Arg Ile Asn Gly Met His Ser Glu Asn Arg Tyr Ser Leu
                 85                  90                  95

Leu Glu Leu Ser Pro Val Glu Val Gly Val Val Ser Leu Tyr Gly Val
                100                 105                 110

Lys Ser Gly Met Phe Val Ala Met Asn Ala Lys Gly Lys Leu Tyr Gly
                115                 120                 125

Ser Arg Tyr Phe Asn Glu Glu Cys Lys Phe Lys Glu Thr Leu Leu Pro
130                 135                 140

Asn Asn Tyr Asn Ala Tyr Glu Ser Arg Lys Tyr Pro Gly Met Tyr Ile
145                 150                 155                 160

Ala Leu Gly Lys Asn Gly Arg Thr Lys Lys Gly Asn Arg Val Ser Pro
                165                 170                 175

Thr Met Thr Leu Thr His Phe Leu Pro Arg Ile
                180                 185
```

<210> SEQ ID NO 12
<211> LENGTH: 198
<212> TYPE: PRT
<213> ORGANISM: Homo sapien

<400> SEQUENCE: 12

```
Met Ser Arg Gly Ala Gly Arg Leu Gln Gly Thr Leu Trp Ala Leu Val
  1               5                  10                  15

Phe Leu Gly Ile Leu Val Gly Met Val Val Pro Ser Pro Ala Gly Thr
                 20                  25                  30

Arg Ala Asn Asn Thr Leu Leu Asp Ser Arg Gly Trp Gly Thr Leu Leu
                 35                  40                  45

Ser Arg Ser Arg Ala Gly Leu Ala Gly Glu Ile Ala Gly Val Asn Trp
 50                  55                  60

Glu Ser Gly Tyr Leu Val Gly Ile Lys Arg Gln Arg Arg Leu Tyr Cys
 65                  70                  75                  80

Asn Val Gly Ile Gly Phe His Leu Gln Val Leu Pro Asp Gly Arg Ile
                 85                  90                  95

Ser Gly Thr His Glu Glu Asn Pro Tyr Ser Leu Leu Glu Ile Ser Thr
                100                 105                 110

Val Glu Arg Gly Val Val Ser Leu Phe Gly Val Arg Ser Ala Leu Phe
                115                 120                 125

Val Ala Met Asn Ser Lys Gly Arg Leu Tyr Ala Thr Pro Ser Phe Gln
130                 135                 140

Glu Glu Cys Lys Phe Arg Glu Thr Leu Leu Pro Asn Asn Tyr Asn Ala
145                 150                 155                 160

Tyr Glu Ser Asp Leu Tyr Gln Gly Thr Tyr Ile Ala Leu Ser Lys Tyr
                165                 170                 175

Gly Arg Val Lys Arg Gly Ser Lys Val Ser Pro Ile Met Thr Val Thr
                180                 185                 190

His Phe Leu Pro Arg Ile
                195
```

<210> SEQ ID NO 13
<211> LENGTH: 219
<212> TYPE: PRT
<213> ORGANISM: Homo sapien -continued

```
<400> SEQUENCE: 13

Met Ser Leu Ser Phe Leu Leu Leu Phe Ser His Leu Ile Leu
  1               5                  10                  15

Ser Ala Trp Ala His Gly Glu Lys Arg Leu Ala Pro Lys Gly Gln Pro
             20                  25                  30

Gly Pro Ala Ala Thr Asp Arg Asn Pro Ile Gly Ser Ser Ser Arg Ser
             35                  40                  45

Ser Ser Ser Ala Met Ser Ser Ser Ala Ser Ser Ser Pro Ala Ala
 50                  55                  60

Ser Leu Gly Ser Gln Gly Ser Gly Leu Glu Gln Ser Ser Phe Gln Trp
 65                  70                  75                  80

Ser Pro Ser Gly Arg Arg Thr Gly Ser Leu Tyr Cys Arg Val Gly Ile
             85                  90                  95

Gly Phe His Leu Gln Ile Tyr Pro Asp Gly Lys Val Asn Gly Ser His
             100                 105                 110

Glu Ala Asn Met Leu Ser Val Leu Glu Ile Phe Ala Val Ser Gln Gly
             115                 120                 125

Ile Val Gly Ile Arg Gly Val Phe Ser Asn Lys Phe Leu Ala Met Ser
 130                 135                 140

Lys Lys Gly Lys Leu His Ala Ser Ala Lys Phe Thr Asp Asp Cys Lys
145                 150                 155                 160

Phe Arg Glu Arg Phe Gln Glu Asn Ser Tyr Asn Thr Tyr Ala Ser Ala
             165                 170                 175

Ile His Arg Thr Glu Lys Thr Gly Arg Glu Trp Tyr Val Ala Leu Asn
             180                 185                 190

Lys Arg Gly Lys Ala Lys Arg Gly Cys Ser Pro Arg Val Lys Pro Gln
             195                 200                 205

His Ile Ser Thr His Phe Leu Pro Arg Phe Lys
         210                 215

<210> SEQ ID NO 14
<211> LENGTH: 190
<212> TYPE: PRT
<213> ORGANISM: Homo sapien

<400> SEQUENCE: 14

Met His Lys Trp Ile Leu Thr Trp Ile Leu Pro Thr Leu Leu Tyr Arg
  1               5                  10                  15

Ser Cys Phe His Ile Ile Cys Leu Val Gly Thr Ile Ser Leu Ala Cys
             20                  25                  30

Asn Asp Met Thr Pro Glu Gln Met Ala Thr Asn Val Asn Cys Ser Ser
             35                  40                  45

Pro Glu Arg His Thr Arg Ser Tyr Asp Tyr Met Glu Gly Gly Asp Ile
 50                  55                  60

Arg Val Arg Arg Leu Phe Cys Arg Thr Gln Trp Tyr Leu Arg Ile Asp
 65                  70                  75                  80

Lys Arg Gly Lys Val Lys Gly Thr Gln Glu Met Lys Asn Asn Tyr Asn
             85                  90                  95

Ile Met Glu Ile Arg Thr Val Ala Val Gly Ile Val Ala Ile Lys Gly
             100                 105                 110

Val Glu Ser Glu Phe Tyr Leu Ala Met Asn Lys Glu Gly Lys Leu Tyr
             115                 120                 125

Ala Lys Lys Glu Cys Asn Glu Asp Cys Asn Phe Lys Glu Leu Ile Leu
 130                 135                 140
```

```
Glu Asn His Tyr Asn Thr Tyr Ala Ser Ala Lys Trp Thr His Asn Gly
145                 150                 155                 160

Gly Glu Met Phe Val Ala Leu Asn Gln Lys Gly Ile Pro Val Arg Gly
                165                 170                 175

Lys Lys Thr Lys Lys Glu Gln Lys Thr Ala His Phe Leu Pro
            180                 185                 190

<210> SEQ ID NO 15
<211> LENGTH: 183
<212> TYPE: PRT
<213> ORGANISM: Mus musculus

<400> SEQUENCE: 15

Met Gly Leu Ile Trp Leu Leu Leu Ser Leu Leu Glu Pro Ser Trp
1               5                   10                  15

Pro Thr Thr Gly Pro Gly Thr Arg Leu Arg Arg Asp Ala Gly Gly Arg
                20                  25                  30

Gly Gly Val Tyr Glu His Leu Gly Gly Ala Pro Arg Arg Arg Lys Leu
            35                  40                  45

Tyr Cys Ala Thr Lys Tyr His Leu Gln Leu His Pro Ser Gly Arg Val
50                  55                  60

Asn Gly Ser Leu Glu Asn Ser Ala Tyr Ser Ile Leu Glu Ile Thr Ala
65                  70                  75                  80

Val Glu Val Gly Val Val Ala Ile Lys Gly Leu Phe Ser Gly Arg Tyr
                85                  90                  95

Leu Ala Met Asn Lys Arg Gly Arg Leu Tyr Ala Ser Asp His Tyr Asn
                100                 105                 110

Ala Glu Cys Glu Phe Val Glu Arg Ile His Glu Leu Gly Tyr Asn Thr
            115                 120                 125

Tyr Ala Ser Arg Leu Tyr Arg Thr Gly Ser Ser Gly Pro Gly Ala Gln
            130                 135                 140

Arg Gln Pro Gly Ala Gln Arg Pro Trp Tyr Val Ser Val Asn Gly Lys
145                 150                 155                 160

Gly Arg Pro Arg Arg Gly Phe Lys Thr Arg Arg Thr Gln Lys Ser Ser
                165                 170                 175

Leu Phe Leu Pro Arg Val Leu
            180

<210> SEQ ID NO 16
<211> LENGTH: 190
<212> TYPE: PRT
<213> ORGANISM: Homo sapien

<400> SEQUENCE: 16

Met Ala Pro Leu Gly Glu Val Gly Asn Tyr Phe Gly Val Gln Asp Ala
1               5                   10                  15

Val Pro Phe Gly Asn Val Pro Val Leu Pro Val Asp Ser Pro Val Leu
                20                  25                  30

Leu Ser Asp His Leu Gly Gln Ser Glu Ala Gly Gly Leu Pro Arg Gly
            35                  40                  45

Pro Ala Val Thr Asp Leu Asp His Leu Lys Gly Ile Leu Arg Arg Arg
50                  55                  60

Gln Leu Tyr Cys Arg Thr Gly Phe His Leu Glu Ile Phe Pro Asn Gly
65                  70                  75                  80

Thr Ile Gln Gly Thr Arg Lys Asp His Ser Arg Phe Gly Ile Leu Glu
                85                  90                  95
```

```
Phe Ile Ser Ile Ala Val Gly Leu Val Ser Ile Arg Gly Val Asp Ser
                100                 105                 110

Gly Leu Tyr Leu Gly Met Asn Glu Lys Gly Glu Leu Tyr Gly Ser Glu
            115                 120                 125

Lys Leu Thr Gln Glu Cys Val Phe Arg Glu Gln Phe Glu Glu Asn Trp
        130                 135                 140

Tyr Asn Thr Tyr Ser Ser Asn Leu Tyr Lys His Val Asp Thr Gly Arg
145                 150                 155                 160

Arg Tyr Tyr Val Ala Leu Asn Lys Asp Gly Thr Pro Arg Glu Gly Thr
                165                 170                 175

Arg Thr Lys Arg His Gln Lys Phe Thr His Phe Leu Pro Arg
            180                 185                 190

<210> SEQ ID NO 17
<211> LENGTH: 167
<212> TYPE: PRT
<213> ORGANISM: Mus musculus

<400> SEQUENCE: 17

Met Gly Ser Pro Arg Ser Ala Leu Ser Cys Leu Leu His Leu Leu
1               5                   10                  15

Val Leu Cys Leu Gln Ala Gln His Val Arg Glu Gln Ser Leu Val Thr
            20                  25                  30

Asp Gln Leu Ser Arg Arg Leu Ile Arg Thr Tyr Gln Leu Tyr Ser Arg
        35                  40                  45

Thr Ser Gly Lys His Val Gln Val Leu Ala Asn Lys Arg Ile Asn Ala
    50                  55                  60

Met Ala Glu Asp Gly Asp Pro Phe Ala Lys Leu Ile Val Glu Thr Asp
65                  70                  75                  80

Thr Phe Gly Ser Arg Val Arg Val Arg Gly Ala Glu Thr Gly Leu Tyr
                85                  90                  95

Ile Cys Met Asn Lys Lys Gly Lys Leu Ile Ala Lys Ser Asn Gly Lys
                100                 105                 110

Gly Lys Asp Cys Val Phe Thr Glu Ile Val Leu Glu Asn Asn Tyr Thr
            115                 120                 125

Ala Leu Gln Asn Ala Lys Tyr Glu Gly Trp Tyr Met Ala Phe Thr Arg
        130                 135                 140

Lys Gly Arg Pro Arg Lys Gly Ser Lys Thr Arg Gln His Gln Arg Glu
145                 150                 155                 160

Val His Phe Met Lys Arg Leu
                165

<210> SEQ ID NO 18
<211> LENGTH: 158
<212> TYPE: PRT
<213> ORGANISM: Artificial Sequence
<220> FEATURE:
<223> OTHER INFORMATION: artificial

<400> SEQUENCE: 18

Met Ala Leu Leu Leu Leu Leu Leu Val Pro Gly Pro Gly Ser Thr Thr
1               5                   10                  15

Thr Asn Asp Ala Leu Leu Glu Ser Arg Gly Ser Ala Ala Arg Asp Leu
            20                  25                  30

Gly Lys Lys Arg Thr Arg Arg Leu Tyr Cys Arg Val Gly Gly Phe His
        35                  40                  45
```

```
                                   -continued

Leu Gln Ile Leu Pro Asp Gly Arg Val Asn Gly Thr His Glu Ser Asn
    50                  55                  60

Arg Tyr Ser Leu Leu Glu Leu Ser Ala Val Glu Val Gly Val Val Ser
65                  70                  75                  80

Ile Lys Gly Val Glu Ser Gly Leu Phe Leu Ala Met Asn Lys Lys Gly
                85                  90                  95

Lys Leu Tyr Ala Ser Lys Lys Phe Thr Glu Glu Cys Lys Phe Lys Glu
            100                 105                 110

Arg Leu Leu Glu Asn Asn Tyr Asn Thr Tyr Ala Ser Ala Lys Tyr Arg
            115                 120                 125

Gly Trp Tyr Val Ala Leu Asn Lys Asn Gly Arg Pro Lys Arg Gly Ser
        130                 135                 140

Lys Thr Ser Pro Thr Gln Lys Ala Thr His Phe Leu Pro Arg
145                 150                 155
```

METHOD OF ISOLATING RECEPTOR AND LIGAND DNA

RELATED APPLICATIONS

This application is a divisional of U.S. Ser. No. 08/776,207, filed on Jun. 23, 1997 (371 [c])(now U.S. Pat. No. 6,080,718, the teachings of which are herein incorporated by reference, and which is the U.S. National Phase of International Application PCT/US95/09172, filed on Jul. 19, 1995, which claims priority to U.S. application Ser. No. 08/441,629, filed on May 15, 1995 (now U.S. Pat. No. 5,766,923), which is a Continuation-in-Part of U.S. Ser. No. 08/279,217, filed on Jul. 22, 1994 (now U.S. Pat. No. 5,573,944).

GOVERNMENT SUPPORT

The work described herein was supported in whole or in part by a grant from the United States Government, NIH POE Number PO1 HL43821, and a grant from the Human Frontier Science Program Organization, Number LT-153/91 (Tour Europe 20, place des Halles 67054 Strasbourg Cedex, France). The United States Government has certain rights in the invention.

BACKGROUND OF THE INVENTION

Transmembrane receptors are proteins which are localized in the plasma membrane of eukaryotic cells. These receptors have an extracellular domain, a transmembrane domain and an intracellular domain. Transmembrane receptors mediate molecular signaling functions by, for example, binding specifically with an external signaling molecule (referred to as a ligand) which activates the receptor. Activation results typically in the triggering of an intracellular catalytic function which is carried out by, or mediated through, the intracellular domain of the transmembrane receptor.

There are various families of transmembrane receptors that show overall similarity in sequence. The highest conservation of sequence is in the intracellular catalytic domain. Characteristic amino acid position can be used to define classes of receptors or to distinguish related family members. Sequences are much more divergent in the extracellular domain.

A variety of methods have been developed for the identification and isolation of transmembrane receptors. This is frequently a straightforward matter since receptors often share a common sequence in their catalytic domain. However, the identification of the ligands which bind to, and activate, the transmembrane receptors is a much more difficult undertaking. Brute force approaches for the identification of ligands for known receptors are rarely successful. Brute force approaches usually depend on a biological activity that can be monitored (e.g., nerve growth for nerve growth factor; or glucose homeostasis for the insulin receptor) or they depend on finding a source of the ligand and using affinity to purify it. In general, however, a source of the ligand is not known, nor is there an obvious or easily assayed biological activity. Therefore, there are many receptors, referred to as "orphan receptors", for which no corresponding ligand has been identified. Further, although several ligands may be known for a specific receptor, it is important to determine the remaining ligands for that receptor to fully understand its role in the growth and maintenance of the vertebrate body. A systematic approach to the identification of receptor ligands would be of great value for the identification of ligands having useful pharmacological activities.

SUMMARY OF THE INVENTION

The present invention relates to compositions and methods which are useful in connection with the identification of transmembrane receptors and their corresponding ligands. Preferred transmembrane receptors include tyrosine kinase receptors, cytokine receptors and tyrosine phosphatase receptors. Such receptors mediate cell signaling through the interaction of specific binding pairs (e.g., receptoligand pairs). The present invention is based on the finding that an unknown component in a receptor-mediated signaling pathway, which results ultimately in an intracellular catalytic event, can be identified by combining other known components within a cellular background within which the catalytic event ordinarily will not take place at significant levels. A cDNA expression library is then used to transform such cells. If the cDNA insert encodes the missing component of the transmembrane receptor-mediated signaling pathway, the catalytic event will be triggered. Detection of the otherwise absent catalytic activity is indicative of a cDNA insert encoding the missing component.

The invention also provides two novel ligands for the FGF receptor. Both the isolated DNA sequences of these ligands (FRL-2 is SEQ ID NO:1 and FRL-1 is SEQ ID NO:3), as well as the isolated polypeptides (SEQ ID NO:2 and SEQ ID NO:4, respectively) encoded by these DNA sequences are described. Other nucleic acids of this invention include nucleotide sequences, both DNA and RNA, that comprise a portion of or all of sequences complementary to the DNA sequences described above. The genes FRL-2 and FRL-1 were formerly designated XT1 (or ALP) and EG2 (or CLP), respectively, in U.S. Pat. No. 5,573,944.

This invention also encompasses agonists (mimics) and antagonists (inhibitors or blocking agents) of the polypeptides described herein. Agonists and antagonists can include antibodies or other polypeptides with amino acid sequences that produce a similar (trigger FGF-mediated phosphorylation) or inhibitory function regarding the binding of the ligand to its FGF receptor.

The compositions of this invention may be used for diagnostic and therapeutic purposes, either alone or in combination with other compounds. Transgenic gene therapy is also provided using the DNA sequences or a fragment thereof in a sense or antisense orientation to affect the function or lack of function of an FGF receptor in vertebrate cells or tissues.

BRIEF DESCRIPTION OF THE DRAWINGS

FIGS. 1A–1B is a diagram illustrating the steps employed in the identification of a ligand specific for the FGF receptor.

FIG. 3 is the nucleotide sequence (SEQ ID NO:1) of a cDNA clone, FRL-2 (ALP), encoding the angiogenin-like ligand.

FIG. 4 is the amino acid sequence (SEQ ID NO:2) of the polypeptide encoded by the nucleotide sequence of FIG. 3.

FIG. 5 is a comparison of the amino acid sequence (SEQ ID NO:2) of the FRL-2 (ALP) gene product compared to bovine angiogenin protein (SEQ ID NO:5) and Chinese hamster pancreatic RNase (SEQ ID NO:6).

FIG. 6 is the nucleotide sequence (SEQ ID NO:3) of a cDNA clone, FRL-1 (CLP), encoding the cripto-like ligand.

FIG. 7 is the amino acid sequence (SEQ ID NO:4) of the polypeptide encoded by the nucleotide sequence of FIG. 6.

FIG. 8 is a comparison of the amino acid sequence (SEQ ID NO:4) of the FRL-1 (CLP) gene product compared to mouse cripto protein (SEQ ID NO:7).

FIGS. 10A–10B is a comparison of the amino acid sequences of human bFGF; bovine aFGF; human Kaposi FGF, Xenopus embryonis FGF; human FGF6; human FGF5; human FGF; mouse int2; human FGF9; and human FGF8 (SEQ ID NOS:8–17, respectively) all of which are known ligands for FGF receptors, to a majority (e.g., consensus) sequence (SEQ ID NO:18.

FIG. 11 shows the predicted cleavage sites, the glycosylation sites, and the hydrophophic regions at the C-terminus of the FRL-1 (CLP) (SEQ ID NO:4) and FRL-2 (ALP) (SEQ ID NO:2) proteins.

FIG. 12 shows the amino acid residues of the FRL-1 (CLP) (SEQ ID NO:4) protein that are highly conserved in the EGF repeat.

DETAILED DESCRIPTION OF THE INVENTION

Figure 1A:
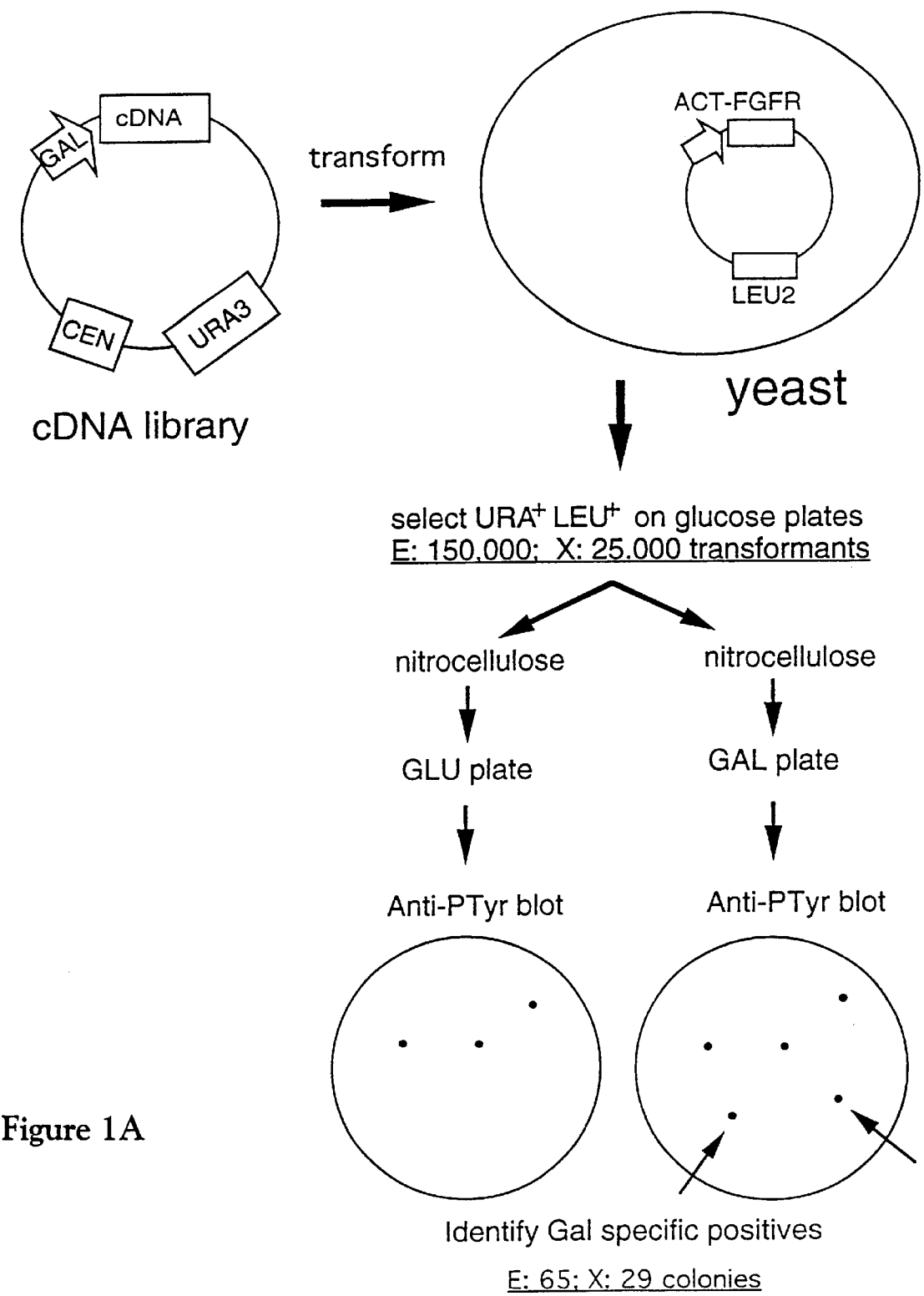

Transmembrane receptors have a binding site with high affinity for a specific signaling molecule. The signaling molecule is referred to herein as a ligand. The present invention is based on the development of a novel approach for the identification of polypeptide ligands by functional expression in the yeast *Sacchuroiiyces cerevisiae*. This approach is based on the previously unproven hypothesis that it may be possible to functionally express a heterologous tyrosine kinase receptor and its corresponding polypeptide ligand in the same yeast cell, leading to the activation of the receptor and a substantial increase in intracellular tyrosine phosphorylation. The intracellular tyrosine kinase activity of the tyrosine kinase receptor is activated by the binding of a ligand to the extracellular domain of the receptor. This interaction can occur on the surface of the cell (plasma membrane) or in intracellular membrane compartments such as secretory vesicles. In either case, according to the hypothesis confined herein, the activation of the cytoplasmically oriented kinase domain results in phosphorylation of tyrosine residues of cytoplasmic protein targets.

Yeast was chosen as an expression system because many molecular biological techniques are available and it has been demonstrated that many higher eukaryotic genes, including some growth factor-encoding genes, can be functionally expressed in yeast. In addition, only a few endogenous protein tyrosine kinases have been identified in yeast, so that yeast is expected to have a low background of endogenous tyrosine phosphorylation. These features enabled the development of a screen to identify polypeptide ligands for heterologous tyrosine kinase receptors for which no ligand has yet been identified. Such receptors are referred to as orphan receptors. The term heterologous is used herein to mean "non-endogenous". Thus, for example, a tyrosine kinase which is heterologous in the yeast *Saccharomyces cerevisiae* is a tyrosine kinase which is non-endogenous (i.e., not present) in wild-type *Saccharomyces cerevisiae*.

The disclosed method for identifying a ligand for a tyrosine kinase receptor involves the co-expression in yeast cells (preferably *Saccharomyces cerevisiae*) of a gene encoding a tyrosine kinase receptor, together with an expression cDNA library which, for example, is constricted from a tissue or cell line that is thought to synthesize a receptor ligand in vivo. The tyrosine kinase gene, together with any regulatory elements required for expression, can be introduced into the yeast strain on a stable plasmid (e.g., a CEN-based plasmid), or it can be integrated into the yeast chromosome using standard techniques (*Methods In Enzymology*, vol. 194, C. Guthrie and G. Fink, eds., (1991).

The choice of expression vectors for use in connection with the cDNA library is not limited to a particular vector. Any expression vector suitable for use in yeast cells is appropriate. The discussion relating to experiments disclosed in the Exemplification section which follows describes a particular combination of elements which was determined to yield meaningful results. However, many options are available for genetic markers, promoters and ancillary expression sequences. As discussed in greater detail below, the use of an inducible promoter to drive expression of the cDNA library is a preferred feature which provides a convenient means for demonstrating that observed changes in tyrosine kinase activity are, in fact, cDNA dependent.

In a preferred format of the assay, two expression constructs are employed; the first expression construct contains the tyrosine kinase gene and the second expression construct carries the cDNA library. Typically the two expression constructs are not introduced simultaneously, but rather a stable yeast strain is first established which harbors the tyrosine kinase receptor carried on a CEN-based plasmid. Other regulatory sequences are included, as needed, to ensure that the tyrosine kinase gene is constitutively expressed. A CEN-based expression vector contains CEN sequences which are specific centromelic relgions which promote equal segregation during cell division. The inclusion of such sequences in the expression construct results in improved mitotic segregation. It has been reported, for example, that mitotic segregation of CEN-based plasmids results in a population of cells in which over 90% of the cells carry one to two copies of the CEN-based plasmid. Faulty mitotic segregation in a similar transformation experiment with an otherwise identical expression construct which lacks CEN sequences would be expected to result in a cell population in which only about 5–20% of the cells contain the plasmid.

Many transmembrane tyrosine kinase receptors have been identified (for reviews see, e.g., Hanks, *Current Opinion in Structural Biology* 1: 369 (1991) and Pawson and Bernstein, *Trends in Genetics* 6: 350 (1990). A number of these tyrosine kinase receptors are orphan receptors for which no activating ligand has been identified. Any transmembrane tyrosine kinase that can be expressed in yeast cells is useful in connection with the present invention. Based on fundamental principles of molecular biology, there is no reason to believe a priori that any member of the tyrosine kinase receptor family would not be useful in connection with the present invention. Preferably, the gene encoding the tyrosine kinase receptor is isolated from the same organism from which nucleic acid is to be isolated for use in the construction of a cDNA library.

As discussed in the Exemplification section which follows, the level of expression of the transmembrane tyrosine kinase is a variable which must be considered in the design of the assay for ligand identification. For example, it was determined that high level expression of the FGF receptor results in a substantial increase in intracellular phosphorylation, even in the absence of FGF. Therefore, it is important that expression of the transmembrane receptor be driven by regulatory elements which result in a sufficient level of expression of the transmembrane receptor to facilitate detection following activation of the receptor by ligand binding, while not resulting in overexpression to the extent that ligand-independent autophosphorylation results. A preferred promoter for the expression of the transmembrane receptor is the ACT1 (actin) promoter. This promoter was determined to provide a robust, ligand-dependent signal in the experiments described below.

The cDNA library is prepared by conventional techniques. Briefly, mRNA is isolated from an organism of interest. An RNA-directed DNA polymerase is employed for first strand synthesis using the mRNA as template. Second strand synthesis is carried out using a DNA-directed DNA polymerase which results in the cDNA product. Following conventional processing to facilitate cloning of the cDNA, the cDNA is inserted into an expression vector suitable for use in yeast cells. Preferably the promoter which drives expression from the cDNA expression construct is an inducible promoter (e.g., GAL1).

As disclosed in the Exemplification section that follows, removal of the endogenous signal sequence from a cDNA insert encoding a functional receptor ligand resulted in inactivation of the ligand. It appeals, therefore, to be necessary to include a signal sequence in the cDNA library constructs to mark the encoded polypeptide for transport across the membrane of the endoplasmic reticulum thereby enabling the extracellular release of the encoded polypeptide which facilitates interaction with the extracellular domain of a transmembrane receptor. The signal sequence employed in the experiments disclosed herein was the signal sequence of Saccharomyces cerevisiae invertase. However, any signal sequence which can function in yeast should be useful in connection with the present invention (Nothwehr and Gordon, *Bioessays* 12: 479 (1990)).

The cDNA expression library is then used to transform the yeast strain which constitutively expresses the transmembrane tyrosine kinase gene. mRNA encoding the tyrosine kinase receptor and the cDNA product arc thought to be translated in the rough endoplasmic reticulum, accumulate in the inner cavity of the rough endoplasmic reticulum, and migrate to the lumen of the Golgi vesicles for transport to the Golgi complex. Within the Golgi complex, proteins are "addressed" for their ultimate destination. From the Golgi complex, the addressed proteins are transported out of the complex by secretory vesicles.

A transmembrane tyrosine kinase receptor, if sequestered in a secretory vesicle, the Golgi complex or the endoplasmic reticulum, is oriented such that the cytoplasmic domain is in contact with the cellular cytoplasm as the various vesicles migrate from the Golgi complex to the plasma membrane which is the ultimate destination for a transmembrane receptor. It is possible that the signal sequence bearing polypeptides encoded by the cDNA library can be co-compartmentalized with the transmembrane receptor in the same secretory vesicle. If this were to occur, any cDNA encoded ligand specific for the tyrosine kinase receptor could bind with the "extracellular" portion of the tyrosine kinase receptor (which is located in the internal portion of the secretory vesicle during the migration to the plasma membrane) thereby activating intracellular tyrosine kinases through contact with the cytoplasmically oriented intracellular domain of the tyrosine kinase receptor. Alternatively, activation of intracellular tyrosine kinase activity could also result from interaction with an extracellular polypeptide encoded by the cDNA library through interaction with a plasma transmembrane tyrosine kinase receptor. This occurs, for example, following, migration of the secretory vesicle to the plasma membrane resulting in the incorporation of the plasma transmembrane tyrosine kinase receptor and export of the signal sequence-bearing cDNA encoded polypeptide ligand.

In either case, activation of the intracellular tyrosine kinase activity results in the phosphorylation of intracellular tyrosine residues at a level which is substantially higher (i.e., at least about 4-fold higher) than background levels of phosphorylation in the yeast stain harboring an expression construct containing only the gene encoding the tyrosine kinase receptor (the negative control strain).

Figure 2:
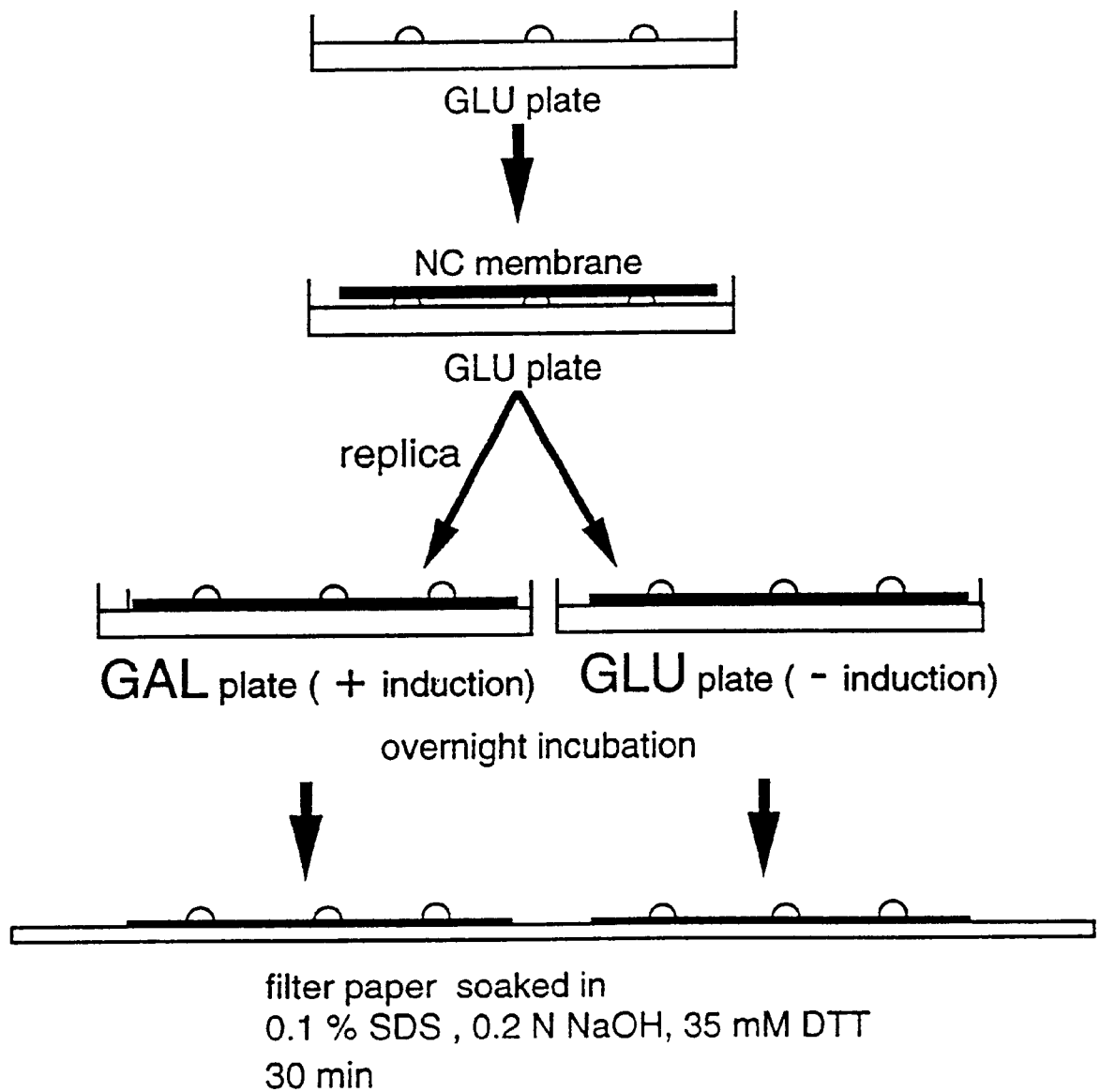
FIG. 2 is a diagram illustrating the colony Western blot technique.

The preferred method for determining the level of intracellular tyrosine phosphorylation is a colony Western blot using replica plates. It will be recognized that, although particularly convenient, the colony Western blot method is but one example of many conventional assays which could be employed to determine levels of intracellular tyrosine kinase activity. The colony Western blot procedure using replica plates is shown diagrammatically in FIG. 2. cDNA library transformants are initially plated on media which do not contain an inducer of the promoter which drives expression of the cDNA insert. For examples, if the GAL1 promoter is used to drive expression of the cDNA insert, cDNA library transformants are initially plated on a medium containing 2% glucose. On this growth medium, cells containing the cDNA expression construct will grow, but the encoded cDNA product is not expressed.

A set of replica filters is produced from the initial transformation plate by sequentially placing a set of directionally oriented membranes (e.g., nitrocellulose filter membranes) over the transformation plate such that the membrane contacts existing transformant colonies. Cells from transformation colonies adhere to the membranes to form a pattern which represents the pattern of colonies on the transformation plate. Each of the replica filters is then placed on a separate plate, one of which contains a compound which will induce the inducible promoter (e.g., 2% galactose to induce the GAL1 promoter) and one of which will not induce the inducible promoter (e.g., 2% glucose for the GAL1 promoter). Both plates are incubated overnight to promote regrowth of the original cDNA library transformants.

Following overnight incubation the replica filters are removed from the growth medium plates, and the colonies are lysed in situ by soaking the replica filters in a lysis solution for a period of time sufficient to lyse cellular membranes (e.g., 0.1% SDS, 0.2 N NaOH, 35 mM DTT for about 30 minutes). The replica filters arc then probed with anti-phosphotyrosine antibodies. Colonies which exhibit elevated tyrosine kinase activity on the replica filter which had been incubated overnight on a growth medium containing a compound which induces expression of the cDNA insert linked to the inducible promoter, but which do not exhibit elevated tyrosine kinase activity on the replica filter incubated overnight on a growth medium lacking the inducing compound, contain a cDNA insert encoding a candidate ligand.

To confirm that a candidate ligand is, in fact, a ligand (and not, for example, a distinct tyrosine kinase), the expression construct is recovered (or rescued) from the cells of the colony demonstrating increased tyrosine kinase activity when grown under inducing conditions. The rescued expression construct is then used to transform a first yeast strain which is known to constitutively express the tyrosine kinase gene, and a second yeast strain which does not express the tyrosine kinase gene. Increased tyrosine kinase activity in the strain which is known to express the tyrosine kinase gene, coupled with no increased tyrosine kinase activity in the strain which does not express the tyrosine kinase gene, serves as confirmation that the cDNA insert of the cDNA expression construct encodes a polypeptide ligand which binds to, and activates, the tyrosine kinase gene product.

Following confirmation that the candidate ligand is, in fact, a receptor ligand, it is a straightforward matter to identify and characterize the polypeptide encoded by the cDNA library which is responsible for the increase in tyrosine kinase activity. This is accomplished by isolating plasmid DNA from the strain which exhibits the elevated tyrosine kinase activity and characterizing the insert carried in the plasmid (e.g., by DNA sequence analysis). The molecule encoded by the cDNA insert can then be further characterized by conventional approaches such as expression and isolation of the encoded polypeptide followed by in vitro binding studies in order to confirm the specificity of the binding interaction with the transmembrane receptor.

The method of the present invention is not limited to the isolation of tyrosine kinase receptor ligands. Rather, the method can be modified for use in the identification of ligands for any transmembrane receptor having a single transmembrane domain, an extracellular domain and an intracellular domain. This is accomplished by generating an expression construct encoding a chimeric fusion protein comprising the extracellular domain of a transmembrane receptor fused to the intracellular domain of a specific tyrosile kinase receptor (e.g., the FGF receptor). As mentioned previously, this construct is preferably generated in a CEN-based plasmid background or, alternatively, in a plasmid which will facilitate integration of the chimeric receptor into the yeast chromosome. Conventional molecular biological techniques are employed to generate this construct, as well as all others disclosed in this specification (see e.g., *Molecular Cloning-A Laboratory Manual*, Sambrook, J., et al., eds., Cold Spring Harbor Publications, Cold Spring Harbor, N.Y. (1989)). This expression construct encoding the tyrosine kinase receptor fusion protein is used in a manner analogous to the expression construct encoding the tyrosine kinase receptor in the embodiment described above.

Briefly, the preferred embodiment of this aspect of the invention includes the construction of a yeast strain which constitutively expresses a chimeric fusion protein of the type described above. This strain is then transformed with a cDNA expression library generated using mRNA isolated from the organism of interest. A ligand which binds specifically to the native transmembrane receptor will bind to the extracellular domain of the tyrosine kinase fusion protein and this ligand binding will trigger ligand-dependent intracellular tyrosine kinase activity mediated by the intracellular domain of the tyrosine kinase receptor. Intracellular tyrosine kinase activity is detected in the manner described previously.

A specific example of this embodiment of the present invention is applicable to the isolation of a ligand for a cytokine receptor (e.,g., erythropoietin receptor, interleukin-3 receptor, etc.). Cytokine receptors, like tyrosine kinase receptors, are transmembrane receptors found in mammalian cells and possess both an extracellular domain and an intracellular domain. However, unlike the tyrosine kinase receptors, cytokine receptors do not possess a catalytic domain but rather recruit cytoplasmic tyrosine kinase enzymes in response to ligand activation. More specifically, the intracellular (cytoplasmic) domain of the cytokine receptor has been shown to bind to, and activate, a class of cytoplasmic tyrosine kinases (e.g., the JAK2/TYK2 class).

To isolate cytokine receptor ligands, a yeast strain is constructed which constitutively expresses a cytoplasmic tyrosine kinase and a transmembrane cytokine receptor. This yeast strain is then transformed with a cDNA expression library from an organism of interest, preferably under the control of an inducible promoter. Elevated levels of tyrosine kinase activity will be observed if the polypeptide encoded by the cDNA library insert functions as a ligand for the native cytokine receptor. Binding of the polypeptide ligand to the extracellular domain of the cytokine receptor (either at the plasma membrane or within a secretory vesicle) results in the activation of the cytoplasmic tyrosine kinase.

The colony Western blot procedure discussed above, and shown diagrammatically in FIG. 2, is the preferred method for screening for an expression construct encoding a functional ligand. Specifically, a set of replica filters is prepared from the original transformation plate and the first and second replica filters are incubated overnight under inducing conditions, and non-inducing conditions, respectively. Colonies affixed to the replica filters arc then lysed and probed with anti-phosphotyrosine antibodies. Increased levels of tyrosine kinase activity can be indicative of a cDNA insert encoding a ligand for the cytokine receptor or, alternatively, a cDNA insert encoding a cytoplasmic tyrosine kinase enzyme. To determine which of these two alternatives is responsible for the observed increase in tyrosine kinase activity, the expression construct encoding, the candidate ligand is rescued and used to independently transform a first cell population which constitutively expresses the cytokine receptor and the cytoplasmic tyrosine kinase, and a second cell population which constitutively expresses the cytokine receptor but not the cytoplasmic tyrosine kinase. Candidates which demonstrate an increase in tyrosine kinase activity in the first cell population, but not the second, encode a cytokine receptor ligand. Expression constructs which result in an increase in tyrosine kinase activity in both the first cell population and the second cell population encode a cytoplasmic tyrosine kinase.

Given the fundamental disclosure that a yeast cell system can be used to identify ligands and other members of specific binding pairs involved in receptor-mediated molecular signaling, numerous variations of the theme described above are derivable through routine experimentation. Using such variations, any single polypeptide component of the receptor-mediated signaling pathway can be identified through the introduction of a cDNA library into yeast cells which have been modified to constitutively produce other necessary components of the signaling pathway.

For example, the methods described above can be modified to facilitate the identification of a cytokine receptor. As discussed above, cytokine-receptor mediated signaling involves a cytokine receptor and a cytoplasmic tyrosine kinase which is activated by interaction with the cytoplasmic domain of the cytokine receptor. As reported in the Exemplification section below, overexpression of the transmembrane tyrosine kinase (e.g., by expression prom the GAL1 promoter) resulted in ligand-independent tyrosine kinase activity. By analogy, it would be expected that overexpression of a transmembrane cytokine receptor in the presence of a cytoplasmic tyrosine kinase would yield ligand-independent tyrosine kinase activity.

More specifically, a yeast strain constitutively expressing a cytoplasmic tyrosine kinase is first constructed. The use of the GAL1 promoter would be expected to result in a high level of cytoplasmic tyrosine kinase expression. However, routine experimentation may be required to optimize the expression level. It is preferred, for example, that the cytoplasmic tyrosine kinase be produced at such a level that it is detectable by Western blot.

A cDNA library is then constructed, preferably with the expression of the cDNA insert under the control of an inducible promoter. Replica filters are produced and incubated independently with, and without, a compound capable of inducing expression from the inducible promoter.

Increased levels of tyrosine kinase activity are detected, for example, by colony Western blot in cells grown under inducing conditions, but not under non-inducing conditions. This would be observed, for example, when the cDNA insert encodes a cytokine receptor. The expression construct is rescued from these cells and introduced independently into yeast cells with, and without, constitutively expressed intracellular tyrosine kinase. Increased tyrosine kinase activity which is dependent upon the constitutively expressed cytoplasmic tyrosine kinase of the host strain indicates that the cDNA insert encodes a cytokine receptor. Increased tyrosine kinase activity which is not dependent upon the constitutively expressed cytoplasmic tyrosine kinase of the host strain is an indication that the cDNA insert encodes a functional tyrosine kinase. If such a cytokine receptor is known or discovered, yeast strains expressing the cytoplasmic tyrosine kinase and the cytokine receptor can be employed in a method for the isolation of a ligand in a manner analogous to the methods described elsewhere in this specification.

Another example of a variation of presently disclosed method is useful for the identification of a receptor for an orphan polypeptide ligand (i.e., a ligand for which no receptor has been previously identified), or for the identification of new receptors for a ligand which is known to interact productively with one or more previously identified receptors. This method incorporates the use of a yeast strain which has been modified to constitutively produce the previously identified ligand or orphan ligand. A cDNA library is introduced and the colony Western blot is employed to identify colonies which exhibit increased tyrosine kinase activity in the induced state. Rescue of the expression construct, followed by retransformation of yeast cells both with and without a constitutively expressed ligand, is used to confirm ligand-dependent activation of tyrosine kinase activity. It will be recognized that the description above relates specifically to a tyrosine kinase-like receptor. The method is easily modified for use with a cytokine receptor by adding constitutive cytoplasmic tyrosine kinase activity to the list of constitutive host cell requirements.

Similarly, the methods of this invention can be used to identify a cytoplasmic tyrosine kinase if a known cytokine receptor and ligand are provided. In this method, the cytokine receptor and ligand are expressed constitutively in a host yeast strain. The cDNA library is provided, and transformants are screened, in the induced and non-induced state, by the replica method discussed above. Candidate cytoplasmic tyrosine kinases are those encoded by an expression construct conferring increased tyrosine kinase activity in the induced state. The cDNA expression construct is rescued from the identified colony and introduced into yeast cells which constitutively express the cytokine receptor and ligand. The rescued construct is also introduced into a yeast strain lacking the cytokine receptor and ligand. Increased activity in the former, but not in the latter, is indicative of a cDNA insert encoding a cytoplasmic tyrosine kinase.

In another aspect of the invention, polypeptide modulators of receptor-mediated tyrosine kinase activity can be isolated. A polypeptide modulator can be, for example, a polypeptide (intracellular or extracellular) which modifies the affinity of the ligand for receptor, or which modifies the activity of the catalytic domain (either integral or recruited). Polypeptide modulators can be isolated by first providing a yeast strain which constitutively expresses a ligand/receptor pair (together with the cytoplasmic tyrosine kinase in the case of a cytokine receptor/ligand pair). The construction of such strains has been discussed in greater detail above. A yeast cell which constitutively expresses the ligand/receptor pair is expected to exhibit a relatively high level of background tyrosine kinase activity when the cDNA library is expressed in both the induced and non-induced state. However, the presence of a cDNA insert encoding a strong modulator (either an up-modulator or a down-modulator) will be determined by a detectable (i.e., at least about 2-fold) change in the level of tyrosine kinase activity in the induced state due to the presence of the polypeptide modulator.

In another aspect of the invention, ligands which specifically activate transmembrane tyrosine phosphatase receptors can be isolated. Transmembrane tyrosine phosphatase receptors arc membrane components which have an intracellular catalytic domain which functions to remove phosphate groups from tyrosine residues. In other words, the tyrosine phosphatase receptor function can be viewed as a catalytic function which reverses the action of a tyrosine kinase (a tyrosine kinase functions by adding a phosphate group to intracellular tyrosine residues). Tyrosine phosphatase receptors have an extracellular domain and, therefore, the existence of extracellular ligands is presumed although none have been isolated to date.

In order to isolate a cDNA fragment encoding a tyrosine phosphatase receptor ligand, it is necessary to first provide a yeast strain which constitutively expresses cellular components necessary to produce a basal level of intracellular tyrosile kinase activity. This can be accomplished, for example, by providing a strain which constitutively expresses appropriate levels of a transmembrane tyrosine kinase receptor, together with its corresponding ligand. Basal levels of tyrosine kinase activity in such a strain are determined using the colony Western blot, for example.

Following a determination of intracellular tyrosine kinase activity, this strain is further modified to express a tyrosine phosphatase receptor. Subsequent to the introduction of the tyrosine phosphatase receptor gene, levels of tyrosine kinase activity are again determined to ensure that there has been no change in the basal level of phosphorylation detected. In the absence of the tyrosine phosphatase receptor ligand, the addition of the expressible tyrosine phosphatase receptor gene to the strain should not affect basal levels of phosphorylation.

Confirmation that the introduction of the tyrosine phosphatase gene does not affect detected phosphorylation levels is followed by the introduction of a cDNA library, preferably under the control of an inducible promoter. Replica filters are produced from the plate of transformants and incubated overnight under either inducing or non-inducing conditions. The levels of intracellular tyrosine phosphorylation are then determined, for example, by the colony Western blotting procedure. Reduced levels of intracellular tyrosine phosphorylation under inducing growth conditions, relative to the levels determined under non-inducing growth conditions, are an indication that the cDNA insert encodes a tyrosine phosphatase ligand which binds to the extracellular domain of the tyrosine phosphatase receptor thereby activating the tyrosine phosphatase activity which functions to reduce intracellular tyrosine phosphorylation thereby reversing the effect of the constitutively expressed tyrosine kinase. The initial indication that the cDNA insert encodes a tyrosine phosphatase ligand can be confirmed by further studies including, for example, demonstration that the observed decrease in phosphorylation is dependent upon entry of the cDNA encoded product into the secretory pathway. Confirmation that a signal sequence is encoded by the cDNA insert is an example of one type of confirmatory experiment.

The methods of the present invention can be further modified for use in the identification of functionally significant domains in a transmembrane receptor or its ligand. This method is carried out, for example, by mutagenizing either the transmembrane receptor or its ligand by conventional site-directed mutagenic techniques. The mutagenized component is then included in an assay of the type described above with a non-mutagenized copy serving as a positive control. Increased intracellular tyrosine phosphorylation in the positive control coupled with a relative decrease in tyrosine phosphorylation (relative to the positive control) in the assay which includes the mutagenized component indicates that the mutagenized amino acid residue(s) are of functional significance.

The FRL-2 (SEQ ID NO:1) and FRL-1 genes (SEQ ID NO:3) encoding the two novel ligands identified by the methods of the present invention were sequenced and the sequences are shown in FIGS. 3 and 6, respectively. This invention provides isolated DNA encoding all or a portion of the FRL-2 or FRL-1 protein ligands, including DNA that comprises (a) SEQ ID NO:1 or SEQ ID NO:3; (b) a portion of the nucleotide sequence of SEQ ID NO:1 or SEQ ID NO:3; (c) a nucleotide sequence that hybridizes to SEQ ID NO:1 or SEQ ID NO:3 under stringent conditions (See, Ausubel, et al. (1994) *Current Protocols in Molecular Biology*, Section 6.4, John Wiley & Sons, N.Y.);

or (d) DNA differing from the DNA sequences of (a), (b) or (c) in codon sequence due to the degeneracy of the genetic code, and which is the functional equivalent of DNA encoding FRL-2 or FRL-1 protein. By "functional equivalent", it is meant that the DNA encodes a polypeptide that demonstrates the biological function of the FRL-2 or FRL-1 protein ligand.

The cDNA encoding these ligands may be radiolabeled, or labeled with enzymes, fluorescent compounds, or other detectable compounds, and used as a probe or primer to isolate other vertebrate FRL-2 or FRL-1 cDNAs by cross-species hybridization. Alternatively, Northern hybridization can be used to screen mRNAs from other vertebrate cell lines to identify a source of mRNA by which a ligand gene can be cloned.

Figure 10A:
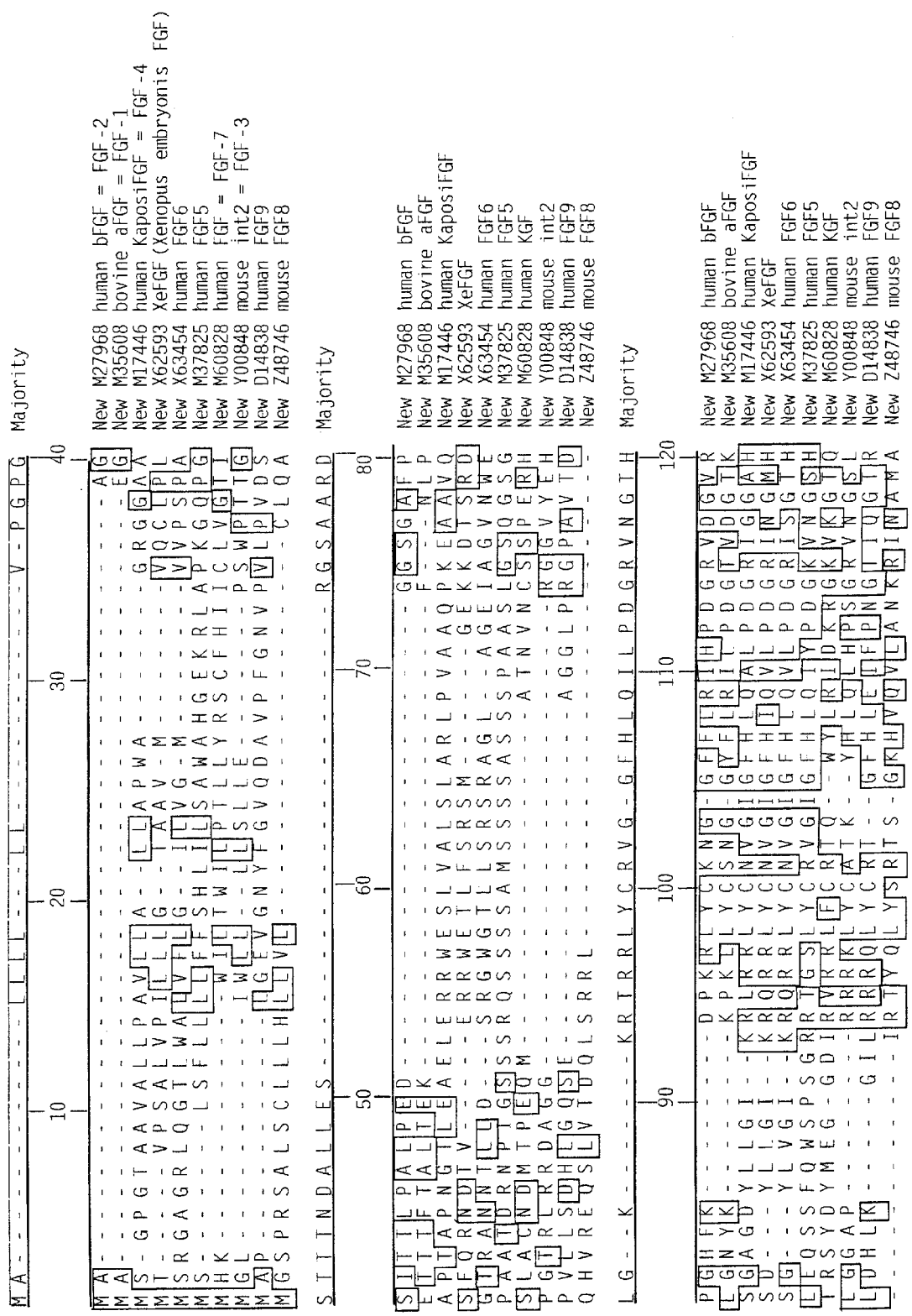
Figure 10B:
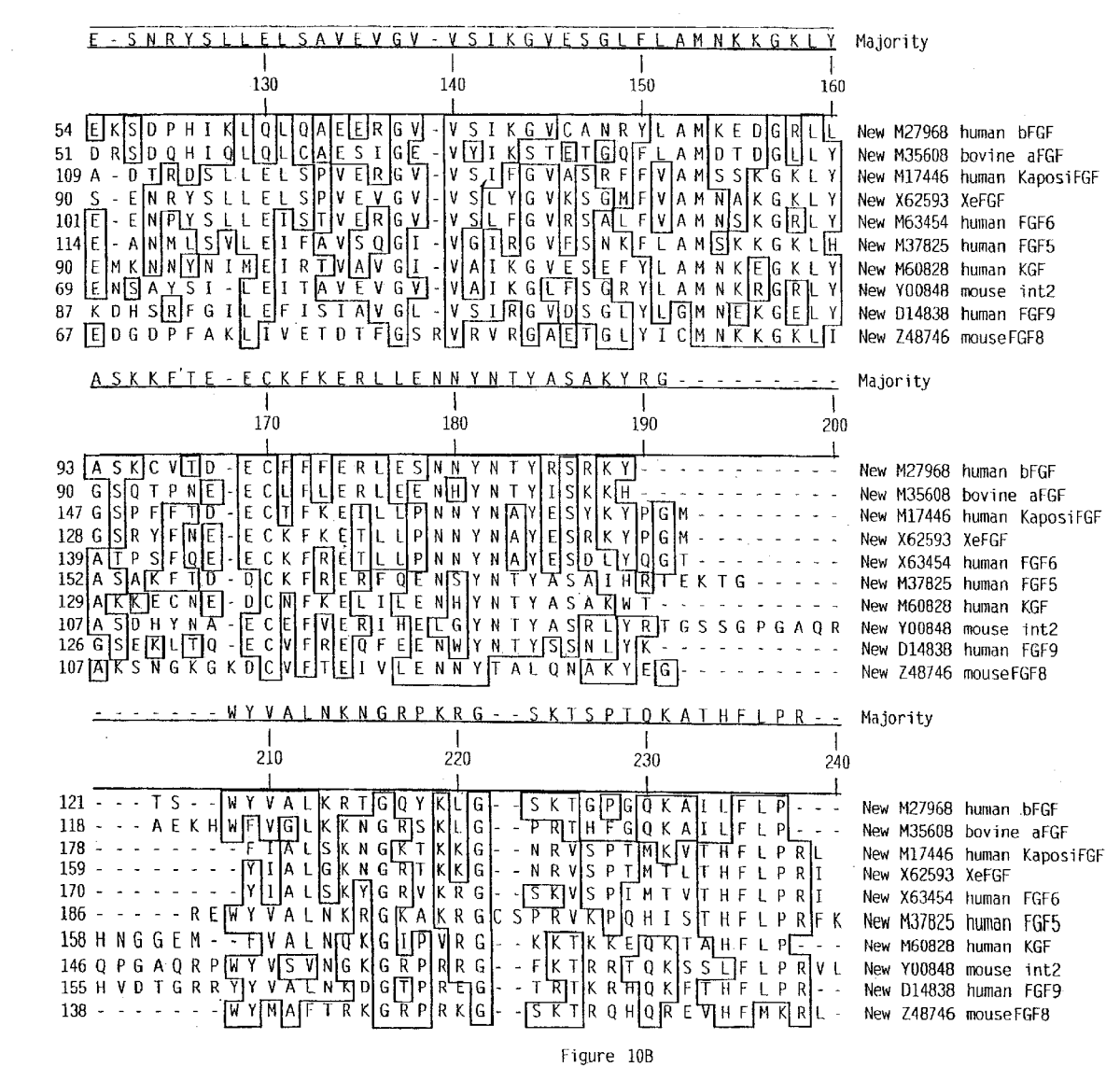

Also provided are the polypeptides comprising the FRL-2 (SEQ ID NO:2) and FRL-1 (SEQ ID NO:4) protein ligands or their functional equivalents, as well as amino acid sequences encoded by the DNA described above. FRL-2 and FRL-1 proteins can be synthesized by synthetically constructing and expressing either SEQ ID NO:1 (for FRL-2) or SEQ ID NO:3 (for FRL-1) using recombinant DNA technology. The degeneracy of the genetic code also permits a wide variety of codon combinations to be used for constructing the DNA chains that encode these polypeptides. The FGF family of receptor ligands contains at least nine members which are structurally closely related to one another. Basilico and Moscatelli (1992) *Adv. Cancer Res.* 59: 115–1165. FIGS. 10–10B is a comparison of the amino acid sequences of known ligands (SEQ ID NOS:8–17, respectively) for FGF receptors showing conserved sequences between these proteins. The FRL-2 and FRL-1 ligands described herein are different structurally and have no conserved (consensus) sequences with the other known FGF ligands.

Growth factors such as FGF are responsible for multiple activities of cells. FGF receptors are expressed in adult tissues and cell lines where they control the proliferation, survival, differentiation, migration or function of cells. Fibroblast growth factor has a broad range of specificity and can stimulate proliferation of many cell types as well as inhibit differentiation of various types of stem cells and act as an inductive signal in embryonic development. The potential for regulating the growth of cells and tissues by stimulating or inhibiting FGF are enormous. Of particular interest is the stimulatory effect of FGF on collateral vascularization and angiogenesis. Such mitogenic effects have stimulated considerable interest in FGF as as a potential therapeutic agent for wound healing, nerve regeneration and cartilage repair.

Accordingly, the possibilities for using the FRL-2 and FRL-1 ligands to modulate the activities of the FGF receptor in cells are manyfold in vertebrates. Further, agonists and antagonists can produce modulating effects. Antagonists can include antisense nucleotide sequences, either DNA or RNA, that are complementary to all or a part of the FRL-2 or FRL-1 gene as well as blocking agents that interfere with the binding of the ligand to the receptor. The antisense sequences can be introduced by means of gene therapy (via infection or transfection) and used to treat individuals who would benefit from reduced levels of FGF receptor activity.

This invention also provides fusion proteins and methods of using fusion proteins to detect and identify sites of FRL-2 and FRL-1 ligand interactions with FGF receptors. Fusion proteins can be applied to detect and assay abnormal expression or to monitor the effects of treatment involving variants or mutants of FRL-2 and FRL-1, as well as agonists and antagonists of FRL-2 and FRL-1 ligands on FGF receptor activity. See, for example, Cheng, H. J. and J. G. Flanaoan (1994) *Cell* 79: 157–68; Flanagan, J. G. and P. Leder (1990) *Cell* 63: 185–94.

Several methods are provided by which the expression of the gene products of FRL-2 or FRL-1 can be detected and quantified. One method for detecting the expression of an FRL-2 or FRL-1 protein ligand in a sample comprises the steps of: (a) treating the sample in a manner that renders mRNA encoding the ligand available for hybridization with a complementary DNA or RNA oligonucleotide, thereby producing a treated sample; contacting the treated sample with at least one DNA or RNA probe which is a nucleotide sequence complementary to all or a portion of the gene or mRNA encoding the ligand; and (c) detecting the hybridization of mRNA from the sample with the probe, wherein hybridization of the mRNA is an indication of the presence of the ligand in the sample. The ligand can be quantified by measuring the extent of hybridization in the sample.

Another method of detecting the level of expression of FRL-2 or FRL-1 protein ligand in a sample comprises the steps of (a) treating the sample in a manner that renders the ligand available for binding to antibodies or antibody fragments specific for the ligand, thereby producing a treated sample; (b) contacting the treated sample with the antibody or antibody fragments under conditions appropriate for formation of antibody-antigen complexes; and (c) detecting the presence of antibody-antigen complexes as an indication of the presence of the ligand in the sample. The level of FRL-2 or FRL-1 protein ligand expression can be quantified in the sample by measuring the amount of antibody-antigen complex as a means to determine the amount of the ligand in the sample.

Antagonists of these ligands can be used to prevent signal transduction of the FGF receptor and thus prevent unwanted resultant cellular responses. For example, a mutated form of SEQ ID NO:1 or SEQ ID NO:3 can be prepared that will encode part or all of a polypeptide that competes with the endogenous polypeptide ligand for binding to its FGF receptor but is not able to trigger phosphorylation. Thus the receptor activities are blocked. This can be useful in preventing tumor growth, for example, where angiogenesis is required for a growing tumor to receive increased nutrients through the blood. Without the increase in vascularization, the tumor is dependent on diffusion of nutrients and is essentially inhibited.

Therefore, in addition to purified FGF receptor ligands, this invention can provide variants and derivatives of native FRL-2 and FRL-1 that retain the desired biological activity (the ability to bind FGF) and modulate the binding of native FRL-2 and FRL-1 to the FGF receptor. A variant, as referred to herein, is a polypeptide which is substantially homologous to a native FGF ligand, but which has an amino acid sequence different from that of the native ligand (from any vertebrate species) because of one or more deletions, insertions or substitutions. Alterations of the native amino acid sequence may be accomplished by any of a number of known techniques. See, for example, *Molecular Cloning-A Laboratory Manual*, Sambrook, J., et al., eds., Cold Spring Harbor Publications, Cold Spring Harbor, N.Y. (1989). Antibodies (either polyclonal or monoclonal) and antibody fragments such as F(ab)$_2$ fragments can be produced that are specific for (bind to) epitopes of FRL-2 or FRL-1 polypeptides. See, for example, Harlow, E. and D. Lane (1988) *Antibodies-A Laboratiorn Manual*, Cold Spring Harbor Press, Cold Spring Harbor Laboratories, N.Y. These antibodies can be used in immunoassays and diagnostically, and can function as antagonists for treatment purposes. The immunoassays can be used to detect and/or quantitate antigens and antibodies where extreme sensitivity is required, and to monitor the progress of treatment in procedures employing modulators of FRL-2 or FRL-1 activity. The antibodies can be labeled or a second antibody that binds to the first antibody can be labeled by some physical or chemical means. The label can be an enzyme which can be assayed, a radioactive substance, a chromophore, or a fluorochrome. E. Harlow and D. Lane (1988), supra.

There are also situations in which one may want to induce or enhance FGF-mediated phosphorylation by increasing either FRL-2 or FRL-1 activity or providing an agonist of either of the ligands in vertebrate cells. The activity of FRL-2 or FRL-1 in vertebrates could be important to the growth, maintenance, and aging of normal cells. Further, modulation of FRL-2 or FRL-1 could be useful to prevent or treat tumor formation. Cells can be treated with FRL-2 or FRL-1 or their agonists, or with mRNA encoding these ligands or agonists to induce or enhance FGF activity resulting in proliferation and/or differentiation of cells.

FGF antagonists have many potential therapeutic applications, such as the treatment of tumors and diseases or disorders of the neural system. FGF antagonists can be combined with a pharmaceutically acceptable diluent, adjuvant or carrier to form a pharmaceutical composition, and can be administered to vertebrates, including humans, either intravenously, subcutaneously, intramuscularly or orally. The required dosage will vary with the particular condition being, treated, with the severity of the condition and with the duration of desired treatment. A therapeutically effective dose is one that will result in a partial or complete reduction of some or all of the adverse symptoms of the disease or disorder.

Angiogenin is a protein of 125 amino acid residues and is able to induce vascularization, including vascularization associated with the growth of tumors. Fett, et al. (1985) *Biochemistry* 24: 5280–5486. The cripto gene product is a protein of 188 amino acid residues that is expressed in undifferentiated teratocarcinoma cells.

Ciccodicola, et al., supra. The cripto gene is expressed differentially in the adult mouse as well as the developing embryo and the regulation of tumor cell growth has been suggested as at least one of its functions. Dono, et al., supra.

Based on the embryonic expression patterns described herein and the knowledge of FGF receptors as prominent receptors in both the embryonic and adult vertebrate body, it is clear that the FRL-2 and FRL-1 gene products express important ligands that modulate growth and differentiation in the adult vertebrate animals. Thus, these genes and their products provide the means by which diseases and disorders of the vertebrate body resulting from excess activity or abnormal lack of activity of an FGF receptor can be detected and treated. Based on the known activities of angiogenin and the expression patterns of cripto, as well as the FRL-2 and FRL-1 temporal patterns of expression during embryogenesis, examples of such activity may include inhibition of tumor growth, induction of neural cell differentiation for repair and regeneration of the central and/or peripheral nervous system, induction of non-neural cell differentiation for repair and regeneration of other organs, and modulation of maintenance and aging of normal cells. These processes can be carried out prenatally as well as in adults.

EXEMPLIFICATION

Disclosed in this Exemplification section are experiments which confirm a previously unproven hypothesis that it may be possible to functionally express a tyrosine kinase receptor and its corresponding polypeptide ligand in the same yeast cell, leading to activation of the receptor and a substantial increase in intracellular tyrosine phosphorylation. More specifically using African clawed frog *Xenopus laevis* FGF receptor and FGF genes as a model system, it has been demonstrated that tyrosine kinase activity is triggered by co-expression of its ligand gene in yeast cells, provided that the ligand is capable of entering the secretory pathway. This activation of FGF receptor was detected by colony Western blotting which enables the screening of a large number of yeast transformants of a cDNA library. By screening a Xenopus cDNA library with a yeast strain expressing FGF receptors two genes encoding novel growth factor-like ligands were identified, which can activate the FGF receptor by conventional pathways.

Materials and Methods i) Yeast strains

A yeast *Saccharomyces cerevisiae* strain used in this study was PSY315 (Mat a, leu2, ura3 his3, lys2).

ii) Yeast transformation and media

The LiCl method (Ito et al. *J. Bacteriol*. 153: 167 (1983)) was used for yeast transformation. Following media were used for yeast culture, YPD (1% yeast extract, 2% tryptone, 2% glucose), YPG (1% yeast extract, 2% tryptone, 2% galactose), SD (0.067% yeast nitrogen base w/o amino acids, 2glucose), and SG (0.067% yeast nitrogen base w/o amino acids, 2% galactose).

iii) Plasmids

The vector plasmids pTS210 and pTS249 carry URA3 and LEU2, respectively, and both carry CEN4, GAL1 promoter and ACT1 terminator. The plasmid pKNA1 harbors LEU2, CEN4, ACT1 promoter and ACT1 terminator.

Two types of plasmids for expression of Xenopus bFGF (basic fibroblast growth factor) in yeast were constructed: One plasmid is constructed by cloning bFGF gene into pTS210 (pTS-FGF) and a second plasmid is identical to the first except that a signal sequence of S. cerevisiae invertase (Carlson et al., *Mol. Cell. Biol.* 3: 439 (1983)) was inserted at the initiation codon of the bFGF gene (pTS-ssFGF). For FGF receptor expression, the Xenopus FGF receptor-1 gene (Musci et al., *Proc. Nacl. Acad. Sci. USA* 87: 8365 (1990)) was cloned into pTS249 and pKNA1 (pTS-FGFR and pKN-FGFR, respectively).

iv) Antibody

Anti-phosphotyrosine antibody 4G10 is purchased from Upstate Biotechnology Incorporated.

v) Colony Western blotting

Yeast transformants were plated on SD plates and incubated at 30° C. for two days. Colonies were transferred onto two nitrocellulose membranes (Millipore HATF 082). These membranes were placed colony-side Lip on SD and SG plates, and incubated overnight at 30° C. The membranes were placed on Whatman 3MM filter paper pre-soaked with lysis buffer (0.1 SDS, 0.2 M NaOH, 35 mM DTT), and incubated at room temperature for 30 min. Colonies on the membranes were rinsed off with water, then the membranes were incubated in TBS-T(20 mM Tris-HCl pH 8.0, 150 mM NaCl, 0.05% Tween-20)-2% BSA (sigma) for blocking on a shaker for one hour, then incubated in 1:1,000-diluted anti-phosphotyrosine antibody (in TBS-T with 2% BSA) for one hour, and subsequently washed three times in TBS-T. The blots were then incubated in 1:10,000-diluted HRP(horse radish peroxidase)-conjugated goat anti-mouse Ig antibody (Bio-Rad) for one hour, and washed three times. Detection was done with chemiluminescence reagents (Amersham, ECL).

vi) cDNA library

The vector plasmid of the cDNA library is λyes (Elledge et al., *Proc. Natl.*

Acad. Sci. USA 88: 1731 (1991)), which carries URA3, CEN4, ARS1, GAL1 promoter and HIS3 terminator. Two sources of cDNA were used for library constriction. One was made from Xenopus XTC cells, The other was made from Xenopus unfertilized eggs and 10 hour embryos.

vii) $Ca^{2+}$ release assay

The procedure for the $Ca^{2+}$ release assay described in Amaya et al. (*Cell* 66: 257 (1991)) was followed. Briefly, oocytes injected with certain mRNAs transcribed in vitro were incubated for two days, then incubated with $^{45}Ca^{2+}$ for three hours. These oocytes were washed in $^{45}Ca^{2+}$-free medium, incubated in media for 10 minutes, followed by scintillation counting of the released radioactivity.

viii) Partial purification of FRL-1 protein

Yeast cells expressing the FRL-1gene under control of GAL promoter were cultured in 1 L of YPG for eight hours (about $2\times10^{10}$ cells). Cells were collected and disrupted with glass beads in 20 ml of buffer A (20 mM Tris-HCl (pH 8.0), 1 mM EDTA, 1 mM PMSF), containing 150 mM NaCl. Cell debris were removed by low speed centrifugation (3,000×g for 5 minutes). The supernatant was centrifuged at 80,000×g for 20 minutes. The pellet was suspended in 5 ml of buffer A containing 1.2 M NaCl, then centrifuged with the same condition. The resulting pellet was suspended in 2 ml of buffer A containing 1% Triton X-100, and centrifuged with the same condition again. The supernatant was diluted 20 fold in modified Barth's saline (Gurdon, *Meth. Cell Biol.* 16: 125 (1977)) containing 0.5 mg/ml BSA.

Results and Discussion

To test whether co-expression of a receptor-tyrosine kinase and its ligand leads to the activation of the kinase in yeast cells, *Xenopus laevis* FGF receptor and bFGF were used as a model system. These genes were co-cxpressed in yeast cells under control of GAL1 promoter by co-transfomiln, pTS-FGFR and pTS-FGF. In addition, bFGF fused with the SUC2 signal sequence (pTS-ssFGF) was also co-cxpressed with the FGF receptor gene because it is known that the bFGF gene does not have a signal sequence.

To determine whether the tyrosiie kiinase is activated in these strains, whole cell extracts were analyzed by immunoblottinog with anti-phosphotyrosine antibody. The following results were obtained: (1) Expression of either bFGF or ssFGF alone had no effect on the level of tyrosine phosphorylation. (2) Expression of the FGF receptor plasmid led to a substantial increase in tyrosiie phosphorylation of several endogenous proteins. (3) Co-expression of FGF receptor and ssFGF dramatically increased tyrosine phosphorylation to a level that was several times higher than the phosphorylation level observed after expression of the FGF receptor alone. (4) Co-cxpression of the FGF receptor and bFGF without a signal sequence did not lead to any increase in phosphorylation above that obtained after expression of the FGF receptor alone, although the same levels of the FGF proteins in the strains expressing the bFGF gene with and without the signal sequence arc detected by immunoblotting with anti-FGF antibody. FGF could not be detected in culture supernatants, suggesting that the interaction was intracellular or periplasmic.

These findings demonstrate that it is possible to functionally co-express the FGF receptor and bFGF in yeast in such a way that they can interact productively in an autocrine manner and thereby lead to an increase in the FGF-receptor mediated phosphorylation of endogenous yeast proteins. bFGF with a signal sequence appears to interact with the extracellular domain of the bFGF receptor on the cell surface or in internal membrane compartments while bFGF without a signal sequence localizes in the cytoplasm and cannot interact with the receptor.

For screening of a large number of yeast transformants, a colony Western blotting method (Lyons and Nelson, *Proc Natl. Acad. Sci. USA* 81: 7426 (1984)) was developed. Yeast transformants expressing bFGF (with or without the signal sequence) and/or FGF receptor were plated on a glucose plate. Colonies were transferred to a filter and the filter was then placed on a galactose plate to induce bFGF expression. After overnight incubation, cells on the filter were lysed and the level of tyrosine phosphorylated proteins in each colony was determined by probing with anti-phosphotyrosine antibodies. The results of this experiment were essentially the same as those described above. That is, expression of the FGF receptor led to an increase in the level of tyrosine phosphorylation that was substantially augmented when bFGF containing a signal sequence was co-expressed, but not when bFGF lacking a signal sequence was co-expressed. These results indicate that the colony Western blotting method is sensitive and can be used to rapidly and easily screen thousands of different yeast colonies.

Several promoters have been tested for the expression of the FGF receptor gene in order to optimize the detection of its activation by colony Western blotting. They included the GAL1, ACT1 (actin; Gallwitz et al., *Nucl. Acids Res.* 9: 6339 (1981)), GPD1 (glyceraldehyde-3-phosphate dehydrogenase; Bitter and Egan, *Gene* 32: 263 (1984)) and TUB1

(α-tubulin; Schatz et al., *Mol. Cell Biol.* 6: 3711 (1986)) promoters. Among them, the ACT1 promoter was determined to be most suitable. FGF receptor gene expression driven by GAL1 promoter proved very high, leading to high levels of tyrosile phosphorylation even in the absence of FGF, while the TUB1 promoter was extremely weak, such that FGF receptor activation by FGF could not be detected. Under the control of the GPD1 promoter, expiession of the FGF receptor gene was repressed by galactose-containing media. On the other hand, the ACT1 promoter gave similar levels of FGF receptor gene expression in galactose- and in glucose-containing media, and levels of tyrosine phosphorylationl were low in the absence of FGF, but significantly increased by expression of ssFCGF. For these reasons, the ACT1 promoter was used for the cDNA screening experiment described below.

The above results encouraged further attempts to use this method to identify novel ligands for tyrosine kinase receptors. As a first step, the method was used to identify new ligands for the FGF receptor. The purpose of this experiment is two-fold: first, to determine whether this system can be used to identify genuine FGF genes, and second, to isolate previously unidentified activators of the FGF receptor.

The procedure followed is outlined diagrammatically in FIG. 1. Yeast cells expressing the FGF receptor were transformed with a cDNA library expected to contain FGF gene family members. Since bFGF (Kimelman et al., *Science* 242: 1053 (1988)), embryonic FGF (Isaacs et al., *Develolpment* 114: 711 (1992)) and int-2/FGF3 (Tannahill, et al., *Development* 115: 695 (1992)) are known to be expressed in Xenopus embryos, we used a cDNA library made from mRNA isolated from Xenopus eggs and embryos (egg library). A library made from XTC cells was also used (XTC library).

150,000 and 25,000 transformants were obtained from the egg and XTC libraries, respectively. In the first screening by colony Western blotting with an anti-phosphotyrosine antibody, 65 and 29 candidates were identified, and by the second screening, nine and two transfomiants were found to be positive (egg and XTC library, respectively). Plasmid DNA in each transformant was rescued, and re-transformed into yeast strains with and without the FGF receptor gene in order to test whether the positive signal is dependent on expression of the FGF receptor gene. Only one plasmid rescued from one of the egg-library transformants was found to be positive even in the absence of the receptor gene expression. The other genes increased tyrosine phosphorylation only when the FGF reccptor gene was co-expressed.

The DNA sequence of the genes present on these plasmids was determined (Table 1). Two genes encoded peptide factors with putative signal peptide sequences.

One gene, designated FRL-2 (FIG. 3, SEQ ID NO:1), encodes a protein (FIG. 4, SEQ ID NO:2), with some homology to bovine angiogenin (SEQ ID NO:5) and Chinese hamster pancreatic ribonuclease A (SEQ ID NO:6) (about 30% identity; (Maes et al., *FEBS Letters* 241: 41 (1988); Haugg and Schein, *Nucl. Acids Res.* 20: 612 (1992)). See FIG. 5. The other gene, FRL-1 (FIG. 6, SEQ ID NO:3), is homologous to cripto, which is an EGF family member, identified in both mouse and human (about 30% identity; Ciccodicola et al., *EMBO J.* 1987–1991(1989); Dono et al., *Development* 118: 1157 (1993)). The FRL-1 gene product (FIG. 7, SEQ ID NO:4) is compared to mouse cripto (SEQ ID NO:7) in FIG. 8. Angiogelnlin, like FGF, is an angiogenesis-promoting factor. Cripto is suggested to have a role in mesoderm by virtue of its embryonic localized induction. Receptors for angiogenin and cripto have not yet been identified. Based on these findings, FRL-2 and FRL-1 gene products are revealed to be novel ligands of the FGF receptor.

The XT2 encodes a putative protease homologous to cathepsin L (58% identity with human cathepsin L; Joseph et al., *J. Clin. Invest.* 81: 1621 (1988); Gal and Gottesman, *Biochem. J.* 253: 303 (1988)). This protease might cleave the FGF receptor in yeast cells, and the cleaved fragment might have an elevated tyrosine kinase activity. EG1 was previously identified in *Xenopus laevis* as a heterogeneous ribonucleoprotein (Kay et al., *Proc. Natl. Acad. Sci. USA* 87: 1367 (1990)). EG3 has an RNA recognition motif found in many RNA binding proteins (Kim and Baker, *Mol. Cell. Biol.* 13: 174 (1993)). These RNA binding protleins might increase synthesis of FGF receptor protein by increasing the efficiency of transcription or translation. Elevated expression induces autophosphorylation.

EG4 encodes a novel 96 kDa protein. Recently, a gene similar to EG4 was found in *C. elegans* (39% identity), but its function is unknown (Wilson et al., *Nature* 368: 32 (1994)). The plasmid which was positive even in the absence of the FGF receptor gene harbored a gene encoding a putative tyrosine kinase homologous to mouse cytoplasmic tyrosine kinase FER (Hao et al., *Mol. Cell. Biol.* 9: 1587 (1989)).

Figure 9:
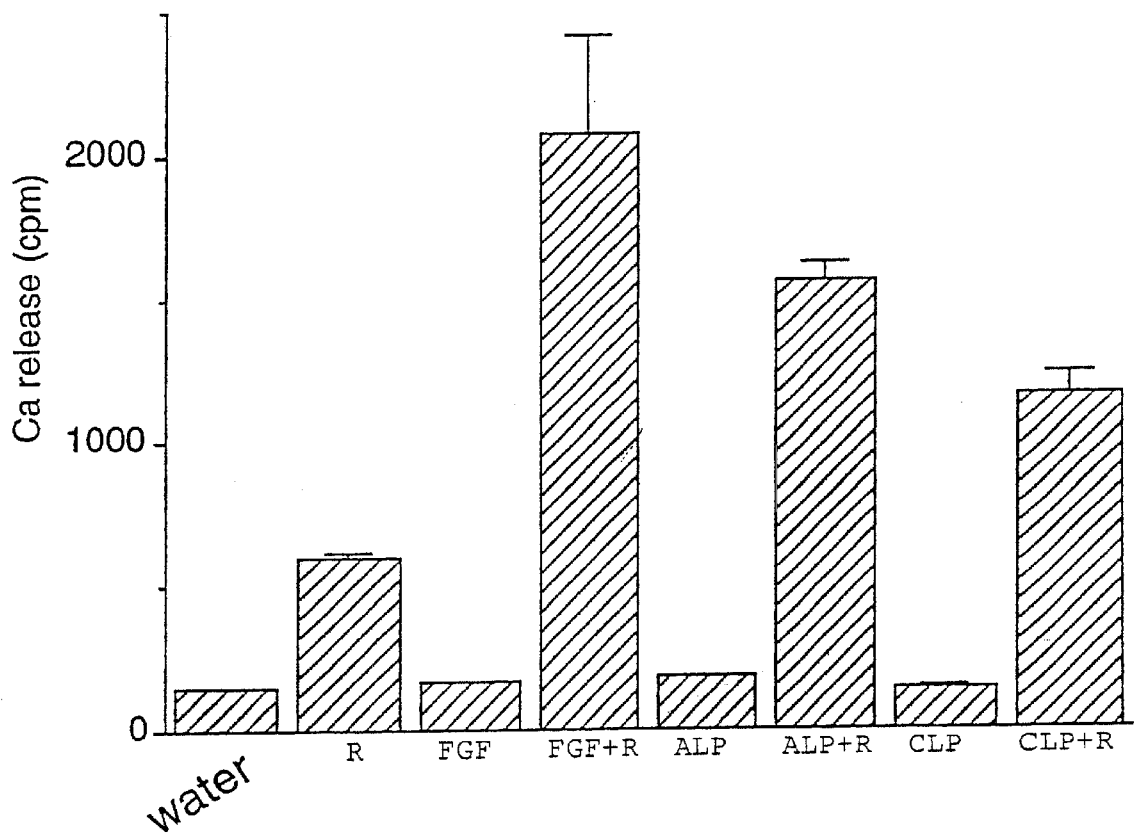
FIG. 9 shows the activation of FGFR by the FRL-2 (ALP) and FRL-1 (CLP) proteins in Xenopus oocytes.

FRL-2 and FRL-1, which have been identified as activators of the FGF receptor in yeast, were tested to determine whether they could also activate the FGF receptor expressed in higher eukaryotic cells. Since it is known that the activation of FGF receptor in Xenopus oocytes is linked to a rapid $Ca^{2+}$ release from internal stores (Johnson et al., *Mol. Cell. Biol.* 10: 4728 (1990)), $Ca^{2+}$ release assays were performed with Xenopus oocytes expressing FGF receptor (FIG. 9).

As for FRL-1, the FRL-1 protein was partially purified tagged with a flag epitope expressed in yeast. The oocytes expressing FGF receptor were labeled with $^{45}Ca^{2+}$ treated with FRL-1, followed by $Ca^{2+}$ release assay. It was found that Ca release was stimulated by treatment of partially puritied FRL-1 protein.

As for FRL-2, this protein has not been expressed efficiently enough to purify the protein, so instead, FRL-2 mRNA was co-injected with FGF receptor mRNA into oocytes. If FRL-2 protein activates the FGF receptor in oocytes, it is expected that the FGF receptor would be constitutively activated by the continuous synthesis of FRL-2 protein, and that the basal level of $Ca^{2+}$ efflux in the co-injected oocyte would be higher than in oocytes injected FGF receptor mRNA alone. $Ca^{2+}$ efflux of labeled oocytes was measured, and it was found that co-injection of FRL-2 and FGF receptor mRNAs increased $Ca^{2+}$ release two-fold more than the injection of FGF receptor message alone. Co-injection of bFGF and FGF receptor mRNA increased $Ca^{2+}$ release three-fold. FRL-2 or bFGF mRNA alone did not increase Ca2+ release.

These results demonstrate that FRL-2 and FRL-1 can activate FGF receptor expressed in Xenopus oocytes, and that these proteins synthesized in vivo can work as activators of FGF receptor.

TABLE 1

Genes Which Increase Protein-Tyrosine Phosphorylation in Yeast Cells Expressing FGF Receptor.

| gene | FGF receptor dependency | gene product | frequency of isolation |
|---|---|---|---|
| 1) secreted proteins | | | |
| FRL-2 | + | homologous to angiogenin and RNaseA | 1 |
| FRL-1 | + | cripto (EGF-like growth factor) | 4 |
| XT2 | + | 58% identical to human cathepsin L | 1 |
| 2) RNA binding proteins | | | |
| EG1 | + | heterogeneous ribonucleoprotein | 2 |
| EG3 | + | RNA binding protein | 1 |
| 3) a novel protein | | | |
| EG4 | + | novel 96 kd protein | 1 |
| 4) FGF-receptor independent | | | |
| EG5 | − | cytoplasmic tyrosine kinase TER | 1 |

The temporal expression patterns of FRL-2 and FRL-1 during embryogenesis both suggest important effects on the embryo. Both ligands induce mesoderm and convergent extention in animal caps. FRL-1 is also able to induce neural tissues in animal caps. FRL-2 is expressed late in development, especially at about stage 27 to about stage 38 of development. (For a description of stages, see Nieucoop and Faber (1994) *Normal Table of Xenopus laevis*, North-Holland Publishing Co., Amsterdam.) This is indicative of strong effects on the formation of the brain, neural tube and somites. FRL-1 is expressed briefly during gastrulation (stages 9 through 13), suggesting a role in the development of the niesoderm and nervous system. Murine cripto transcripts show a very restricted expression pattern during embryogenesis, first in the epiblastic cells that give rise to the mesoderm, then in the forming mesoderm, and later in the developing heart. Dono, et al. (1993) *Development* 118: 1157–1168.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method for identifying a product of interest comprising:
   a) providing a cDNA expression library from an organism of interest, the inserts e.g. being under the control of an inducible promoter;
   b) providing a population of yeast cells that express (e.g. constitutively) a DNA sequence;
   c) transforming the population of yeast cells with the cDNA expression library; and
   d) detecting protein kinase activity in clonally-derived yeast cells as an indication of the presence of DNA encoding the product of interest, wherein the product of interest is:
      (I) a ligand for a tyrosine kinase receptor, and the DNA sequence is a copy of a gene encodinig a heterologous tyrosine kinase receptor, or
      (II) a heterologous tyrosine kinase receptor which is activated by binding to a known polypeptide ligand and the DNA sequence encodes the known polypeptide ligand, or
      (III) a ligand for a transmembrane receptor and the DNA sequence encodes a fusion protein comprising the extracellular domain of the transmembrane receptor fused to the intracellular domain of a tyrosine kinase receptor, or
      (IV) a ligand for a cytokine receptor and the DNA sequence encodes a fusion protein comprising the extracellular domain of the cytokine receptor fused to the intracellular domain of a tyrosine kinase receptor, or
      (V) a cytokine receptor that is activated by binding to a known polypeptide ligand and the DNA sequence encodes a polypeptide ligand and a cytoplasmic tyrosine kinase.

2. A method of claim 1 wherein the DNA sequence is carried on a CEN-based plasmid or inserted into a yeast chromosome.

3. A method for identifying a ligand for a tyrosine phosphatase receptor, comprising;
   a) providing a yeast cell population that constitutively expresses a tyrosine kinase receptor; a polypeptide ligand which binds to and activates the tyrosine kinase receptor; and a tyrosine phosphatase receptor;
   b) transforming the yeast cell population of step a) with a cDNA library from an organism of interest; and
   c) detecting a decrease in intracellular tyrosine phosphorylation in the transformed yeast cell population of step b) relative to an otherwise identical yeast cell population that does not express the cDNA library.

4. A method for identifying a modulator of tyrosine kinase receptor mediated tyrosine kinase activity, comprising:
   a) providing a yeast cell population that constitutively expresses a tyrosine kinase receptor and a polypeptide ligand that binds to and activates the tyrosine kinase receptor;
   b) providing a cDNA library from an organism of interest;
   c) transforming the yeast cells with the cDNA expression library; and
   d) detecting a modulation in intracellular tyrosine kinase activity of at least 2-fold when compared with tyrosine kinase activity from an other wise identical yeast strain which does not express the cDNA library.

* * * * *